United States Patent
Sahin et al.

(10) Patent No.: US 12,378,531 B2
(45) Date of Patent: Aug. 5, 2025

(54) USE OF RNA FOR REPROGRAMMING SOMATIC CELLS

(71) Applicants: BioNTech SE, Mainz (DE); TRON—Translationale Onkologie an der Universitatsmedizin der Johannes Gutenberg Universitat Mainz gemeinnutzige GmbH, Mainz (DE)

(72) Inventors: Ugur Sahin, Mainz (DE); Marco Poleganov, Frankfurt (DE); Tim Beissert, Griesheim (DE)

(73) Assignee: BIONTECH SE, Mainz (DE)

( * ) Notice: Subject to any disclaimer, the term of this patent is extended or adjusted under 35 U.S.C. 154(b) by 641 days.

(21) Appl. No.: 17/241,651

(22) Filed: Apr. 27, 2021

(65) Prior Publication Data

US 2021/0324341 A1    Oct. 21, 2021

Related U.S. Application Data

(63) Continuation of application No. 16/250,366, filed on Jan. 17, 2019, now Pat. No. 11,008,550, which is a continuation of application No. 15/485,601, filed on Apr. 12, 2017, now abandoned, which is a continuation of application No. 14/933,840, filed on Nov. 5, 2015, now abandoned, which is a continuation of application No. 12/735,060, filed as application No. PCT/EP2008/010593 on Dec. 12, 2008, now abandoned.

(30) Foreign Application Priority Data

Dec. 14, 2007    (EP) ..................................... 07024312

(51) Int. Cl.
    *C12N 5/074*    (2010.01)

(52) U.S. Cl.
    CPC ...... *C12N 5/0696* (2013.01); *C12N 2501/602* (2013.01); *C12N 2501/603* (2013.01); *C12N 2501/604* (2013.01); *C12N 2501/606* (2013.01); *C12N 2510/00* (2013.01)

(58) Field of Classification Search
    CPC ............ C12N 5/0696; C12N 2501/602; C12N 2501/603; C12N 2501/604; C12N 2501/606; C12N 2510/00; A61P 43/00
    USPC ......................................................... 435/461
    See application file for complete search history.

(56) References Cited

U.S. PATENT DOCUMENTS 8,058,065 B2 * 11/2011 Yamanaka ........... C12N 5/0696
                                                     435/373

FOREIGN PATENT DOCUMENTS

WO    WO-2008097926 A2 *    8/2008    ............. A61K 35/15

* cited by examiner

*Primary Examiner* — Valarie E Bertoglio
(74) *Attorney, Agent, or Firm* — Olson & Cepuritis, Ltd.

(57) ABSTRACT

Methods for effecting the de-differentiation of somatic cells to cells having stem cell characteristics, in particular pluripotency, include the steps of introducing RNA encoding factors inducing the de-differentiation of somatic cells into the somatic cells and culturing the somatic cells allowing the cells to de-differentiate.

9 Claims, 19 Drawing Sheets

Specification includes a Sequence Listing.

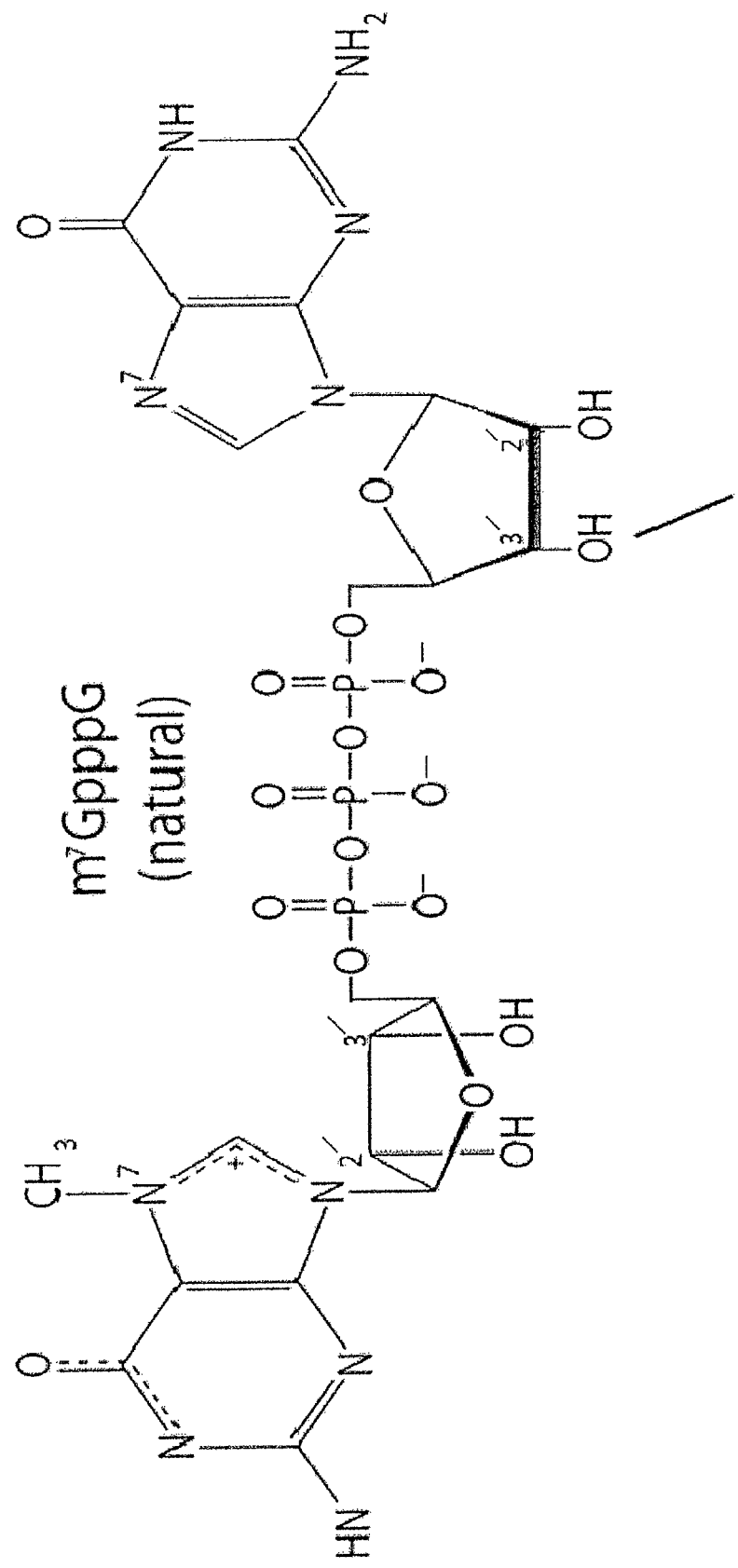
Fig. 4A1

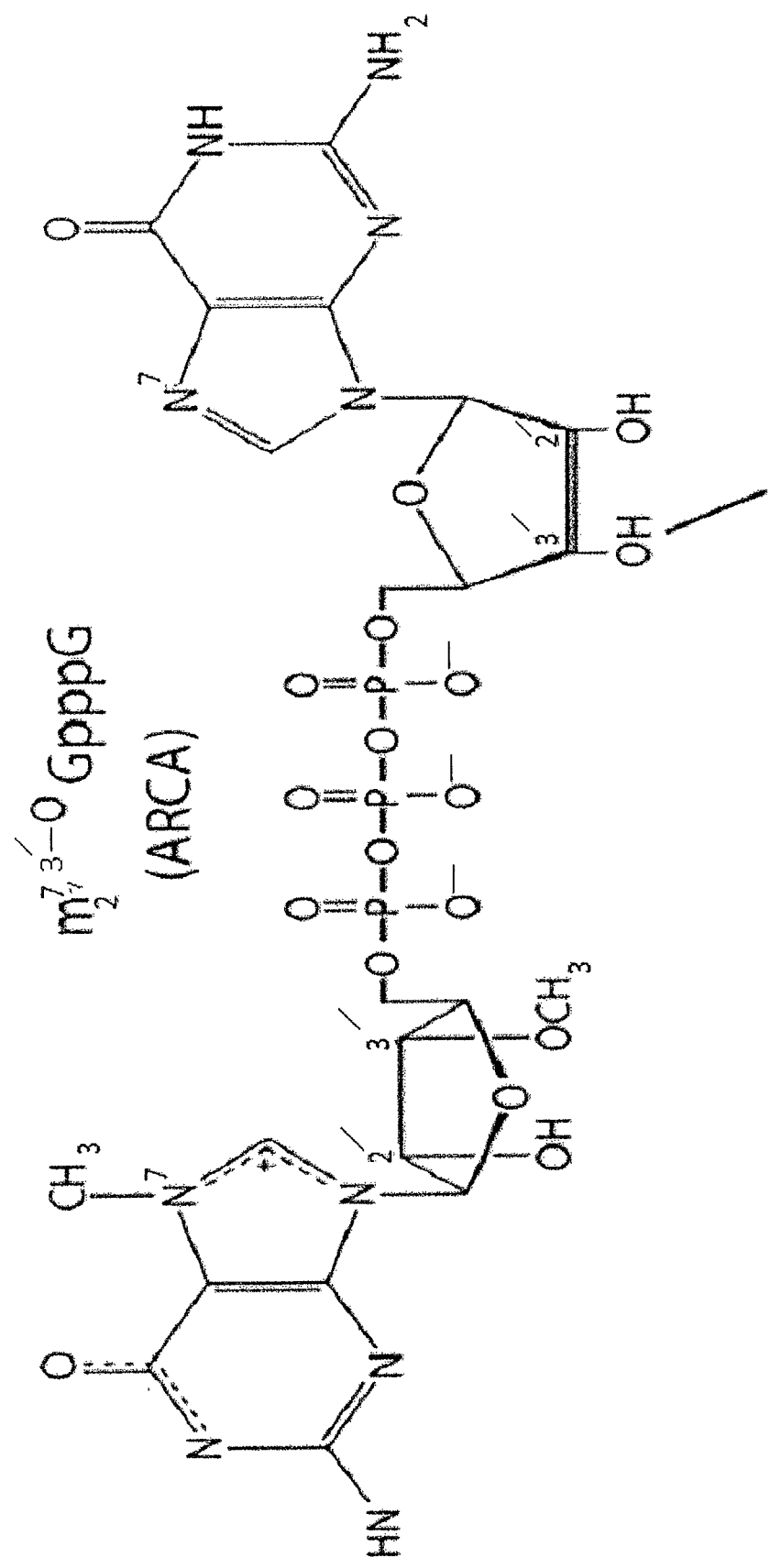
Fig. 4A2

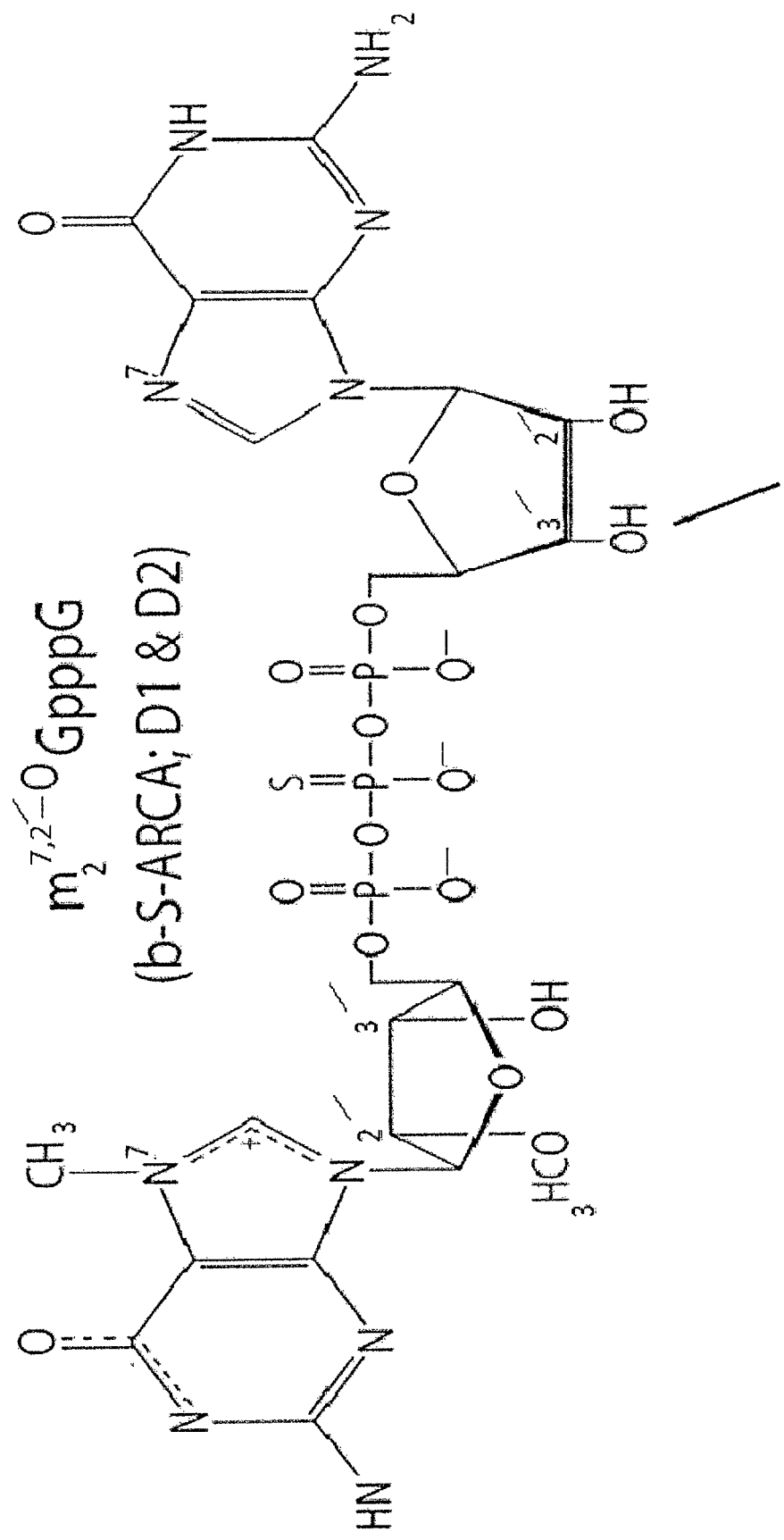
Fig. 4A3

```
                          SEQUENCE LISTING

<160> NUMBER OF SEQ ID NOS: 12

<210> SEQ ID NO 1
<211> LENGTH: 1411
<212> TYPE: DNA
<213> ORGANISM: Homo sapiens

<400> SEQUENCE: 1
ccttcgcaag ccctcatttc accaggcccc cggcttgggg cgccttcctt ccccatggcg      60
ggacacctgg cttcggattt cgccttctcg cccccctccag gtggtggagg tgatgggcca    120 gggggccgg agccgggctg ggttgatcct cggacctggc taagcttcca aggccctcct     180 ggaggggccag gaatcgggcc ggggggttggg ccaggctctg aggtgtgggg gattcccca     240 tgcccccgc cgtatgagtt ctgtgggggg atggcgtact gtgggcccca ggttggagtg      300
gggctagtgc cccaaggcgg cttggagacc tctcagcctg agggcgaagc aggagtcggg    360
gtggagagca actccgatgg ggcctccccg gagccctgca ccgtcacccc tggtgccgtg      420
aagctggaga aggagaagct ggagcaaaac ccggaggagt cccaggacat caaagctctg      480
cagaaagaac tcgagcaatt tgccaagctc ctgaagcaga gaggatcac cctgggatat      540 acacaggccg atgtggggct caccctgggg gttctatttg ggaaggtatt cagccaaacg      600
accatctgcc gctttgaggc tctgcagctt agcttcaaga acatgtgtaa gctgcggccc      660
ttgctgcaga agtgggtgga ggaagctgac aacaatgaaa atcttcagga gatatgcaaa      720
gcagaaaccc tcgtgcaggc ccgaaagaga agcgaacca gtatcgagaa ccgagtgaga      780
ggcaacctgg agaatttgtt cctgcagtgc ccgaaaccca cactgcagca gatcagccac      840
atcgcccagc agcttgggct cgagaaggat gtggtccgag tgtggttctg taaccggcgc      900
cagaagggca agcgatcaag cagcgactat gcacaacgag aggattttga ggctgctggg      960
tctcctttct caggggggacc agtgtccttt cctctgcccc cagggcccca ttttggtacc     1020
ccaggctatg ggagccctca cttcactgca ctgtactcct cggtcccttt ccctgagggg    1080
gaagcctttc ccctgtctc cgtcaccact ctgggctctc ccatgcattc aaactgaggt     1140
gcctgccctt ctaggaatgg gggacagggg gagggggagga gctagggaaa gaaaacctgg     1200
agtttgtgcc agggttttg ggattaagtt cttcattcac taaggaagga attgggaaca      1260
caaagggtgg gggcagggga gttgggggca actggttgga gggaaggtga agttcaatga      1320
tgctcttgat tttaatccca catcatgtat cactttttc ttaaataaag aagcctggga       1380
cacagtagat agacacactt aaaaaaaaaa a                                     1411

<210> SEQ ID NO 2
<211> LENGTH: 360
<212> TYPE: PRT
<213> ORGANISM: Homo sapiens

<400> SEQUENCE: 2

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30
```

```
Arg Thr Trp Leu Ser Phe Gln Gly Pro Pro Gly Pro Gly Ile Gly
             35                  40                  45
Pro Gly Val Gly Pro Gly Ser Glu Val Trp Gly Ile Pro Pro Cys Pro
 50                  55                  60
Pro Pro Tyr Glu Phe Cys Gly Met Ala Tyr Cys Gly Pro Gln Val
 65              70                  75                  80
Gly Val Gly Leu Val Pro Gln Gly Gly Leu Glu Thr Ser Gln Pro Glu
                 85                  90                  95
Gly Glu Ala Gly Val Gly Val Glu Ser Asn Ser Asp Gly Ala Ser Pro
            100                 105                 110
Glu Pro Cys Thr Val Thr Pro Gly Ala Val Lys Leu Glu Lys Glu Lys
            115                 120                 125
Leu Glu Gln Asn Pro Glu Glu Ser Gln Asp Ile Lys Ala Leu Gln Lys
130                 135                 140
Glu Leu Glu Gln Phe Ala Lys Leu Leu Lys Gln Lys Arg Ile Thr Leu
145                 150                 155                 160
Gly Tyr Thr Gln Ala Asp Val Gly Leu Thr Leu Gly Val Leu Phe Gly
                165                 170                 175
Lys Val Phe Ser Gln Thr Thr Ile Cys Arg Phe Glu Ala Leu Gln Leu
            180                 185                 190
Ser Phe Lys Asn Met Cys Lys Leu Arg Pro Leu Leu Gln Lys Trp Val
            195                 200                 205
Glu Glu Ala Asp Asn Asn Glu Asn Leu Gln Glu Ile Cys Lys Ala Glu
210                 215                 220
Thr Leu Val Gln Ala Arg Lys Arg Lys Arg Thr Ser Ile Glu Asn Arg
225                 230                 235                 240
Val Arg Gly Asn Leu Glu Asn Leu Phe Leu Gln Cys Pro Lys Pro Thr
                245                 250                 255
Leu Gln Gln Ile Ser His Ile Ala Gln Gln Leu Gly Leu Glu Lys Asp
            260                 265                 270
Val Val Arg Val Trp Phe Cys Asn Arg Arg Gln Lys Gly Lys Arg Ser
            275                 280                 285
Ser Ser Asp Tyr Ala Gln Arg Glu Asp Phe Glu Ala Ala Gly Ser Pro
290                 295                 300
Phe Ser Gly Gly Pro Val Ser Phe Pro Leu Ala Pro Gly Pro His Phe
305                 310                 315                 320
Gly Thr Pro Gly Tyr Gly Ser Pro His Phe Thr Ala Leu Tyr Ser Ser
                325                 330                 335
Val Pro Phe Pro Glu Gly Glu Ala Phe Pro Pro Val Ser Val Thr Thr
            340                 345                 350
Leu Gly Ser Pro Met His Ser Asn
            355                 360

<210> SEQ ID NO 3
<211> LENGTH: 1085
<212> TYPE: DNA
<213> ORGANISM: Homo sapiens

<400> SEQUENCE: 3
cacagcgccc gcatgtacaa catgatggag acggagctga agccgccggg cccgcagcaa     60
acttcggggg gcggcggcgg caactccacc gcggcggcgg ccggcggcaa ccagaaaaac    120
agcccggacc gcgtcaagcg gcccatgaat gccttcatgg tgtggtcccg cgggcagcgg    180
cgcaagatgg cccaggagaa ccccaagatg cacaactcga gatcagcaa gcgcctgggc    240
```

```
gccgagtgga aacttttgtc ggagacggag aagcggccgt tcatcgacga ggctaagcgg    300
ctgcgagcgc tgcacatgaa ggagcacccg gattataaat accggcccg  gcggaaaacc    360 aagacgctca tgaagaagga taagtacacg ctgcccggcg ggctgctggc ccccggcggc    420
aatagcatgg cgagcggggt cggggtgggc gccggcctgg gcgcgggcgt gaaccagcgc    480
atggacagtt acgcgcacat gaacggctgg agcaacggca gctacagcat gatgcaggac    540
cagctgggct acccgcagca cccgggcctc aatgcgcacg gcgcagcgca gatgcagccc    600
atgcaccgct acgacgtgag cgccctgcag tacaactcca tgaccagctc gcagacctac    660
atgaacggct cgcccaccta cagcatgtcc tactcgcagc agggcacccc tggcatggct    720
cttggctcca tgggttcggt ggtcaagtcc gaggccagct ccagcccccc tgtggttacc    780
tcttcctccc actccagggc gccctgccag gccggggacc tccgggacat gatcagcatg    840
tatctccccg gcgccgaggt gccggaaccc gccgccccca gcagacttca catgtcccag    900
cactaccaga gcggcccggt gcccggcacg gccattaacg gcacactgcc cctctcacac    960
atgtgagggc cggacagcga actggagggg ggagaaattt tcaaagaaaa acgagggaaa   1020
tgggaggggt gcaaaagagg agagtaagaa acagcatgga gaaaacccgg tacgctcaaa   1080
aaaaa                                                               1085
```

<210> SEQ ID NO 4
<211> LENGTH: 317
<212> TYPE: PRT
<213> ORGANISM: Homo sapiens

<400> SEQUENCE: 4

```
Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220
```

```
Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Val Val Thr
            245                 250                 255

Ser Ser Ser His Ser Arg Ala Pro Cys Gln Ala Gly Asp Leu Arg Asp
                260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315

<210> SEQ ID NO 5
<211> LENGTH: 2098
<212> TYPE: DNA
<213> ORGANISM: Homo sapiens

<400> SEQUENCE: 5
attataaatc tagagactcc aggattttaa cgttctgctg gactgagctg gttgcctcat      60
gttattatgc aggcaactca ctttatccca atttcttgat acttttcctt ctggaggtcc     120
tatttctcta acatcttcca gaaaagtctt aaagctgcct taaccttttt tccagtccac     180
ctcttaaatt ttttcctcct cttcctctat actaacatga gtgtggatcc agcttgtccc     240
caaagcttgc cttgctttga agcatccgac tgtaaagaat cttcacctat gcctgtgatt     300
tgtgggcctg aagaaaacta ccatccttg caaatgtctt ctgctgagat gcctcacacg     360
gagactgtct ctcctcttcc ttcctccatg gatctgctta ttcaggacag ccctgattct     420
tccaccagtc ccaaaggcaa acaacccact tctgcagaga gagtgtcgc aaaaaaggaa      480
gacaaggtcc cggtcaagaa acagaagacc agaactgtgt tctcttccac ccagctgtgt     540
gtactcaatg atagatttca gagacagaaa tacctcagcc tccagcagat gcaagaactc     600
tccaacatcc tgaacctcag ctacaaacag gtgaagacct ggttccagaa ccagagaatg     660
aaatctaaga ggtggcagaa aaacaactgg ccgaagaata gcaatggtgt gacgcagaag     720
gcctcagcac ctacctaccc cagcctttac tcttcctacc accagggatg cctggtgaac     780
ccgactggga accttccaat gtggagcaac cagacctgga caattcaac ctggagcaac      840
cagacccaga catccagtc ctggagcaac cactcctgga cactcagac tggtgcacc       900
caatcctgga caatcaggc ctggaacagt cccttctata actgtggaga ggaatctctg      960
cagtcctgca tgcagttcca gccaaattct cctgccagtg acttggaggc tgccttggaa    1020
gctgctgggg aaggccttaa tgtaatacag cagaccacta ggtatttag tactccacaa     1080
accatggatt tattcctaaa ctactccatg aacatgcaac ctgaagacgt gtgaagatga    1140
gtgaaactga tattactcaa tttcagtctg acactggct gaatccttcc tctcccctcc     1200
tcccatccct cataggattt tccttgtttg gaaaccacgt gttctggttt ccatgatgcc     1260
catccagtca atctcatgga gggtggagta tggttggagc ctaatcagcg aggtttcttt     1320
ttttttttt ttcctattgg atcttcctgg agaaaatact tttttttttt ttttttttga     1380
aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
```

| | | |
|---|---|---|
| tgtgttagcc aggatggtct cgatctcctg accttgtgat ccacccgcct cggcctccct | 1620 |
| aacagctggg atttacaggc gtgagccacc gcgccctgcc tagaaaagac attttaataa | 1680 |
| ccttggctgc cgtctctggc tatagataag tagatctaat actagtttgg atatctttag | 1740 |
| ggtttagaat ctaacctcaa gaataagaaa tacaagtaca aattggtgat gaagatgtat | 1800 |
| tcgtattgtt tgggattggg aggctttgct tattttttaa aaactattga ggtaaagggt | 1860 |
| taagctgtaa catacttaat tgatttctta ccgtttttgg ctctgttttg ctatatcccc | 1920 |
| taatttgttg gttgtgctaa tctttgtaga aagaggtctc gtatttgctg catcgtaatg | 1980 |
| acatgagtac tgctttagtt ggtttaagtt caaatgaatg aaacaactat ttttcctttta | 2040 |
| gttgatttta ccctgatttc accgagtgtt tcaatgagta aatatacagc ttaaacat | 2098 |

<210> SEQ ID NO 6
<211> LENGTH: 305
<212> TYPE: PRT
<213> ORGANISM: Homo sapiens

<400> SEQUENCE: 6

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
            290                 295                 300
Val
305

<210> SEQ ID NO 7
<211> LENGTH: 780
<212> TYPE: DNA
<213> ORGANISM: Homo sapiens

<400> SEQUENCE: 7

```
gtgcggggga agatgtagca gcttcttctc cgaaccaacc ctttgccttc ggacttctcc    60
ggggccagca gccgcccgac caggggcccg ggccacgggg ctcagccgac gaccatgggc   120
tccgtgtcca accagcagtt tgcaggtggc tgcgccaagg cggcagaaga ggcgcccgag   180
gaggcgccgg aggacgcggc ccgggcggcg gacgagcctc agctgctgca cggtgcgggc   240
atctgtaagt ggttcaacgt gcgcatgggg ttcggcttcc tgtccatgac cgcccgcgcc   300
ggggtcgcgc tcgaccccccc agtggatgtc tttgtgcacc agagtaagct gcacatggaa   360
gggttccgga gcttgaagga gggtgaggca gtggagttca cctttaagaa gtcagccaag   420
ggtctggaat ccatccgtgt caccggacct ggtggagtat tctgtattgg gagtgagagg   480
cggccaaaag gaaagagcat gcagaagcgc agatcaaaag gagacaggtg ctacaactgt   540
ggaggtctag atcatcatgc caaggaatgc aagctgccac cccagcccaa gaagtgccac   600
ttctgccaga gcatcagcca tatggtagcc tcatgtccgc tgaaggccca gcagggccct   660
agtgcacagg gaaagccaac ctactttcga gaggaagaag aagaaatcca cagccctacc   720
ctgctcccgg aggcacagaa ttgagccaca atgggtgggg ctattctttt gctatcagg    780
```

<210> SEQ ID NO 8
<211> LENGTH: 209
<212> TYPE: PRT
<213> ORGANISM: Homo sapiens

<400> SEQUENCE: 8

Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
                20                  25                  30

Asp Glu Pro Gln Leu Leu His Gly Ala Gly Ile Cys Lys Trp Phe Asn
            35                  40                  45

Val Arg Met Gly Phe Gly Phe Leu Ser Met Thr Ala Arg Ala Gly Val
        50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

```
Cys His Phe Cys Gln Ser Ile Ser His Met Val Ala Ser Cys Pro Leu
            165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn

<210> SEQ ID NO 9
<211> LENGTH: 2639
<212> TYPE: DNA
<213> ORGANISM: Homo sapiens

<400> SEQUENCE: 9
```

| | | | | | |
|---|---|---|---|---|---|
| tcgaggcgac | cgcgacagtg | gtggggacg | ctgctgagtg | aagagagcg | cagcccggcc | 60 |
| accggaccta | cttactcgcc | ttgctgattg | tctattttg | cgtttacaac | ttttctaaga | 120 |
| acttttgtat | acaaaggaac | ttttaaaaa | agacgcttcc | aagttatatt | taatccaaag | 180 |
| aagaaggatc | tcggccaatt | tggggttttg | ggttttggct | tcgtttcttc | tcttcgttga | 240 |
| ctttggggtt | caggtgcccc | agctgcttcg | ggctgccgag | gaccttctgg | gccccccacat | 300 |
| taatgaggca | gccacctggc | gagtctgaca | tggctgtcag | cgacgcgctg | ctcccatctt | 360 |
| tctccacgtt | cgcgtctggc | ccggcggaa | gggagaagac | actgcgtcaa | gcaggtgccc | 420 |
| cgaataaccg | ctggcgggag | gagctctccc | acatgaagcg | acttccccca | gtgcttcccg | 480 |
| gccgccccta | tgacctggcg | gcggcgaccg | tggccacaga | cctggagagc | ggcggagccg | 540 |
| gtgcggcttg | cggcggtagc | aacctggcgc | ccctacctcg | gagagagacc | gaggagttca | 600 |
| acgatctcct | ggacctggac | tttattctct | ccaattcgct | gacccatcct | ccggagtcag | 660 |
| tggccgccac | cgtgtcctcg | tcagcgtcag | cctcctcttc | gtcgtcgccg | tcgagcagcg | 720 |
| gccctgccag | cgcgccctcc | acctgcagct | tcacctatcc | gatccgggcc | gggaacgacc | 780 |
| cgggcgtggc | gccgggcggc | acgggcggag | gcctcctcta | tggcagggag | tccgctcccc | 840 |
| ctccgacggc | tcccttcaac | ctggcggaca | tcaacgacgt | gagcccctcg | ggcggcttcg | 900 |
| tggccgagct | cctgcggcca | gaattggacc | cggtgtacat | tccgccgcag | cagccgcagc | 960 |
| cgccaggtgg | cgggctgatg | ggcaagttcg | tgctgaaggc | gtcgctgagc | gcccctggca | 1020 |
| gcgagtacgg | cagcccgtcg | gtcatcagcg | tcagcaaagg | cagccctgac | ggcagccacc | 1080 |
| cggtggtggt | ggcgccctac | aacggcgggc | cgccgcgcac | gtgccccaag | atcaagcagg | 1140 |
| aggcggtctc | ttcgtgcacc | cacttgggcg | ctggaccccc | tctcagcaat | ggccaccggc | 1200 |
| cggctgcaca | cgacttcccc | ctggggcggc | agctccccag | caggactacc | ccgaccctgg | 1260 |
| gtcttgagga | agtgctgagc | agcagggact | gtcaccctgc | cctgccgctt | cctcccggct | 1320 |
| tccatcccca | cccggggccc | aattacccat | ccttcctgcc | cgatcagatg | cagccgcaag | 1380 |
| tcccgccgct | ccattaccaa | gagctcatgc | caccccggttc | ctgcatgcca | gaggagccca | 1440 |
| agccaaagag | gggaagacga | tcgtggcccc | ggaaaaggac | cgccacccac | acttgtgatt | 1500 |
| acgcgggctg | cggcaaaacc | tacacaaaga | gttcccatct | caaggcacac | ctgcgaaccc | 1560 |
| acacaggtga | gaaccttac | cactgtgact | gggacggctg | tggatggaaa | ttcgcccgct | 1620 |
| cagatgaact | gaccaggcac | taccgtaaac | acacggggca | ccgcccgttc | cagtgccaaa | 1680 |
| aatgcgaccg | agcattttcc | aggtcggacc | acctcgcctt | acacatgaag | aggcatttt | 1740 |
| aaatcccaga | cagtggatat | gacccacact | gccagaagag | aattcagtat | tttttacttt | 1800 |

-continued

```
tcacactgtc ttcccgatga gggaaggagc ccagccagaa agcactacaa tcatggtcaa  1860
gttcccaact gagtcatctt gtgagtggat aatcaggaaa atgaggaat ccaaaagaca   1920
aaaatcaaag aacagatggg gtctgtgact ggatcttcta tcattccaat tctaaatccg  1980
acttgaatat tcctggactt acaaaatgcc aaggggtga ctggaagttg tggatatcag   2040
ggtataaatt atatccgtga gttggggag ggaagaccag aattcccttg aattgtgtat   2100
tgatgcaata taagcataaa agatcacctt gtattctctt taccttctaa agccattat   2160
tatgatgtta gaagaagagg aagaaattca ggtacagaaa acatgtttaa atagcctaaa  2220
tgatggtgct tggtgagtct tggttctaaa ggtaccaaac aaggaagcca agttttcaa   2280
actgctgcat actttgacaa ggaaaatcta tatttgtctt ccgatcaaca tttatgacct  2340
aagtcaggta atatacctgg tttacttctt tagcatttt atgcagacag tctgttatgc   2400
actgtggttt cagatgtgca ataatttgta caatggttta ttcccaagta tgccttaagc  2460
agaacaaatg tgttttcta tatagttcct tgccttaata aatatgtaat ataaatttaa   2520
gcaaacgtct attttgtata tttgtaaact acaaagtaaa atgaacattt tgtggagttt  2580
gtattttgca tactcaaggt gagaattaag ttttaaataa acctataata ttttatctg   2639
```

<210> SEQ ID NO 10  
<211> LENGTH: 470  
<212> TYPE: PRT  
<213> ORGANISM: Homo sapiens
<400> SEQUENCE: 10

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
                85                  90                  95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Pro Ser
        115                 120                 125

Ser Ser Gly Pro Ala Ser Ala Pro Ser Thr Cys Ser Phe Thr Tyr Pro
    130                 135                 140

Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Gly Phe Val Ala
            180                 185                 190

Glu Leu Leu Arg Pro Glu Leu Asp Pro Val Tyr Ile Pro Pro Gln Gln
        195                 200                 205

Pro Gln Pro Pro Gly Gly Gly Leu Met Gly Lys Phe Val Leu Lys Ala
    210                 215                 220

Ser Leu Ser Ala Pro Gly Ser Glu Tyr Gly Ser Pro Ser Val Ile Ser
```

```
                225                 230                 235                 240
Val Ser Lys Gly Ser Pro Asp Gly Ser His Pro Val Val Ala Pro
                245                 250                 255

Tyr Asn Gly Gly Pro Pro Arg Thr Cys Pro Lys Ile Lys Gln Glu Ala
            260                 265                 270

Val Ser Ser Cys Thr His Leu Gly Ala Gly Pro Pro Leu Ser Asn Gly
        275                 280                 285

His Arg Pro Ala Ala His Asp Phe Pro Leu Gly Arg Gln Leu Pro Ser
    290                 295                 300

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
            340                 345                 350

Pro Leu His Tyr Gln Glu Leu Met Pro Pro Gly Ser Cys Met Pro Glu
        355                 360                 365

Glu Pro Lys Pro Lys Arg Gly Arg Arg Ser Trp Pro Arg Lys Arg Thr
    370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
            420                 425                 430

Glu Leu Thr Arg His Tyr Arg Lys His Thr Gly His Arg Pro Phe Gln
        435                 440                 445

Cys Gln Lys Cys Asp Arg Ala Phe Ser Arg Ser Asp His Leu Ala Leu
    450                 455                 460

His Met Lys Arg His Phe
465                 470

<210> SEQ ID NO 11
<211> LENGTH: 2377
<212> TYPE: DNA
<213> ORGANISM: Homo sapiens

<400> SEQUENCE: 11 accccccgagc tgtgctgctc gcggccgcca ccgccgggcc ccggccgtcc ctggctcccc     60
tcctgcctcg agaagggcag ggcttctcag aggcttggcg ggaaaaagaa cggagggagg    120
gatcgcgctg agtataaaag ccggttttcg gggctttatc taactcgctg tagtaattcc    180
agcgagaggc agaggagcg agcgggcggc cggctagggt ggaagagccg ggcgagcaga    240
gctgcgctgc gggcgtcctg ggaagggaga tccggagcga ataggggggct tcgcctctgg    300 cccagccctc ccgctgatcc cccagccagc ggtccgcaac ccttgccgca tccacgaaac    360
tttgcccata gcagcgggcg ggcactttgc actggaactt acaacacccg agcaaggacg    420
cgactctccc gacgcgggga ggctattctg cccatttggg acacttccc cgccgctgcc    480 aggacccgct tctctgaaag gctctccttg cagctgctta cgactggat tttttcggg     540 tagtggaaaa ccagcagcct cccgcgacga tgcccctcaa cgttagcttc accaacagga    600
actatgacct cgactacgac tcggtgcagc cgtatttcta ctgcgacgag gaggagaact    660
tctaccagca gcagcagcag agcgagctgc agccccggc gcccagcgag gatatctgga    720
```

| | |
|---|---|
| agaaattcga gctgctgccc accccgcccc tgtcccctag ccgccgctcc gggctctgct | 780 |
| cgccctccta cgttgcggtc acacccttct cccttcgggg agacaacgac ggcggtggcg | 840 |
| ggagcttctc cacggccgac cagctggaga tggtgaccga gctgctggga ggagacatgg | 900 |
| tgaaccagag tttcatctgc gacccggacg acgagacctt catcaaaaac atcatcatcc | 960 |
| aggactgtat gtggagcggc ttctcggccg ccgccaagct cgtctcagag aagctggcct | 1020 |
| cctaccaggc tgcgcgcaaa gacagcggca gcccgaaccc cgcccgcggc cacagcgtct | 1080 |
| gctccacctc cagcttgtac ctgcaggatc tgagcgccgc cgcctcagag tgcatcgacc | 1140 |
| cctcggtggt cttcccctac cctctcaacg acagcagctc gcccaagtcc tgcgcctcgc | 1200 |
| aagactccag cgccttctct ccgtcctcgg attctctgct ctcctcgacg gagtcctccc | 1260 |
| cgcagggcag ccccgagccc ctggtgctcc atgaggagac accgccacc accagcagcg | 1320 |
| actctgagga ggaacaagaa gatgaggaag aaatcgatgt tgtttctgtg gaaagaggc | 1380 |
| aggctcctgg caaaaggtca gagtctggat caccttctgc tggaggccac agcaaacctc | 1440 |
| ctcacagccc actggtcctc aagaggtgcc acgtctccac acatcagcac aactacgcag | 1500 |
| cgcctccctc cactcggaag gactatcctg ctgccaagag ggtcaagttg acagtgtca | 1560 |
| gagtcctgag acagatcagc aacaaccgaa atgcaccag ccccaggtcc tcggacaccg | 1620 |
| aggagaatgt caagaggcga acacacaacg tcttggagcg ccagaggagg aacgagctaa | 1680 |
| aacgagcttt ttttgccctg cgtgaccaga tcccggagtt ggaaaacaat gaaaaggccc | 1740 |
| ccaaggtagt tatccttaaa aaagccacag catacatcct gtccgtccaa gcagaggagc | 1800 |
| aaaagctcat ttctgaagag gacttgttgc ggaaacgacg agaacagttg aaacacaaac | 1860 |
| ttgaacagct acggaactct tgtgcgtaag gaaaagtaag gaaaacgatt ccttctaaca | 1920 |
| gaaatgtcct gagcaatcac ctatgaactt gtttcaaatg catgatcaaa tgcaacctca | 1980 |
| caaccttggc tgagtcttga gactgaaaga tttagccata atgtaaactg cctcaaattg | 2040 |
| gactttgggc ataaaagaac ttttttatgc ttaccatctt tttttttct ttaacagatt | 2100 |
| tgtatttaag aattgttttt aaaaaatttt aagatttaca caatgtttct ctgtaaatat | 2160 |
| tgccattaaa tgtaaataac tttaataaaa cgtttatagc agttacacag aatttcaatc | 2220 |
| ctagtatata gtacctagta ttataggtac tataaaccct aatttttttt atttaagtac | 2280 |
| attttgcttt ttaaagttga ttttttttcta ttgttttttag aaaaaataaa ataactggca | 2340 |
| aatatatcat tgagccaaaa aaaaaaaaaa aaaaaaa | 2377 |

<210> SEQ ID NO 12
<211> LENGTH: 454
<212> TYPE: PRT
<213> ORGANISM: Homo sapiens

<400> SEQUENCE: 12

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80
```

```
Arg Ser Gly Leu Cys Ser Pro Ser Tyr Val Ala Val Thr Pro Phe Ser
                85              90              95
Leu Arg Gly Asp Asn Asp Gly Gly Gly Ser Phe Ser Thr Ala Asp
            100             105             110
Gln Leu Glu Met Val Thr Glu Leu Leu Gly Gly Asp Met Val Asn Gln
            115             120             125
Ser Phe Ile Cys Asp Pro Asp Glu Thr Phe Ile Lys Asn Ile Ile
130             135             140
Ile Gln Asp Cys Met Trp Ser Gly Phe Ser Ala Ala Lys Leu Val
145             150             155             160
Ser Glu Lys Leu Ala Ser Tyr Gln Ala Ala Arg Lys Asp Ser Gly Ser
            165             170             175
Pro Asn Pro Ala Arg Gly His Ser Val Cys Ser Thr Ser Ser Leu Tyr
            180             185             190
Leu Gln Asp Leu Ser Ala Ala Ser Glu Cys Ile Asp Pro Ser Val
            195             200             205
Val Phe Pro Tyr Pro Leu Asn Asp Ser Ser Ser Pro Lys Ser Cys Ala
            210             215             220
Ser Gln Asp Ser Ser Ala Phe Ser Pro Ser Ser Asp Ser Leu Leu Ser
225             230             235             240
Ser Thr Glu Ser Ser Pro Gln Gly Ser Pro Glu Pro Leu Val Leu His
            245             250             255
Glu Glu Thr Pro Pro Thr Thr Ser Ser Asp Ser Glu Glu Glu Gln Glu
            260             265             270
Asp Glu Glu Glu Ile Asp Val Val Ser Val Glu Lys Arg Gln Ala Pro
            275             280             285
Gly Lys Arg Ser Glu Ser Gly Ser Pro Ser Ala Gly Gly His Ser Lys
            290             295             300
Pro Pro His Ser Pro Leu Val Leu Lys Arg Cys His Val Ser Thr His
305             310             315             320
Gln His Asn Tyr Ala Ala Pro Pro Ser Thr Arg Lys Asp Tyr Pro Ala
            325             330             335
Ala Lys Arg Val Lys Leu Asp Ser Val Arg Val Leu Arg Gln Ile Ser
            340             345             350
Asn Asn Arg Lys Cys Thr Ser Pro Arg Ser Ser Asp Thr Glu Glu Asn
            355             360             365
Val Lys Arg Arg Thr His Asn Val Leu Glu Arg Gln Arg Arg Asn Glu
            370             375             380
Leu Lys Arg Ser Phe Phe Ala Leu Arg Asp Gln Ile Pro Glu Leu Glu
385             390             395             400
Asn Asn Glu Lys Ala Pro Lys Val Val Ile Leu Lys Lys Ala Thr Ala
            405             410             415
Tyr Ile Leu Ser Val Gln Ala Glu Glu Gln Lys Leu Ile Ser Glu Glu
            420             425             430
Asp Leu Leu Arg Lys Arg Arg Glu Gln Leu Lys His Lys Leu Glu Gln
            435             440             445
Leu Arg Asn Ser Cys Ala
    450
```

USE OF RNA FOR REPROGRAMMING SOMATIC CELLS

CROSS-REFERENCE TO RELATED APPLICATIONS

This application is a continuation of U.S. patent application Ser. No. 16/250,366 filed on Jan. 17, 2019, which in turn is a continuation of U.S. patent application Ser. No. 15/485,601, filed on Apr. 12, 2017, which is a continuation of U.S. patent application Ser. No. 14/933,840, filed on Nov. 5, 2015, which is a continuation of U.S. patent application Ser. No. 12/735,060, filed on Nov. 24, 2010, now abandoned, which is the National Stage of International Patent Application No. PCT/EP2008/010593, filed on Dec. 12, 2008, which claims priority of European Patent Application No. 07024312.6, filed on Dec. 14, 2007, each of which is incorporated herein by reference.

INCORPORATION OF SEQUENCE LISTING

This application includes biological sequence information, which is set forth in an ASCII text file having the file name "VOS-128-CON-3_SEQ.txt", created on Jan. 17, 2019, and having a file size of 32,591 bytes, which is incorporated herein by reference.

FIELD OF THE INVENTION

The present invention provides methods for de-differentiating somatic cells into stem-like cells without generating embryos or fetuses. More specifically, the present invention provides methods for effecting the de-differentiation of somatic cells to cells having stem cell characteristics, in particular pluripotency, by introducing RNA encoding factors inducing the de-differentiation of somatic cells into the somatic cells and culturing the somatic cells allowing the cells to de-differentiate. After being de-differentiated, the cells can be induced to re-differentiate into the same or a different somatic cell type such as neuronal, hematopoietic, muscle, epithelial, and other cell types. The stem-like cells derived by the present invention have medical applications for treatment of degenerative diseases by "cell therapy" and may be utilized in novel therapeutic strategies in the treatment of cardiac, neurological, endocrinological, vascular, retinal, dermatological, muscular-skeletal disorders, and other diseases.

BACKGROUND OF THE INVENTION

Stem cells also called progenitor cells are cells with abilities to self-renew, to remain undifferentiated, and to become differentiated into one or more specialized cell types with mature phenotypes. Stem cells are not terminally differentiated and they are not at the end of a differentiation pathway.

Totipotent cells contain all the genetic information needed to create all the cells of the body, including the cells of the placenta. Human cells have this totipotent capacity only during the first few divisions of a fertilized egg. After three to four divisions of totipotent cells, there follows a series of stages in which the cells become increasingly specialized. The next stage of division results in pluripotent cells, which are highly versatile and can give rise to any cell type except the cells of the placenta or other supporting tissues of the uterus. At the next stage, cells become multipotent, meaning they can give rise to several other cell types, but those types are limited in number. At the end of the long chain of cell divisions that make up the embryo are "terminally differentiated" cells that are considered to be permanently committed to a specific function.

There are three main groups of stem cells: (i) adult or somatic stem cells (post-natal), which exist in all post-natal organisms, (ii) embryonic stem cells, which can be derived from a pre-embryonic or embryonic developmental stage and (iii) fetal stem cells (pre-natal), which can be isolated from the developing fetus.

Stem cell technologies involving the isolation and use of human embryonic stem cells have become an important subject of medical research. Human embryonic stem cells have a potential to differentiate into any and all of the cell types in the human body, including complex tissues. It is expected that many diseases resulting from the dysfunction of cells may be amenable to treatment by the administration of human embryonic stem cells or human embryonic stem cell-derived cells. The ability of pluripotent embryonic stem cells to differentiate and give rise to a plurality of specialized mature cells reveals the potential application of these cells as a means to replace, restore, or complement damaged or diseased cells, tissues, and organs. However, scientific and ethical considerations have slowed the progress of research using embryonic stem cells recovered from aborted embryos or embryos formed using in vitro fertilization techniques.

Adult stem cells are present only at low frequencies and exhibit restricted differentiation potential and poor growth. A further problem associated with using adult stems cells is that these cells are not immunologically privileged, or can lose their immunological privilege after transplant, wherein the term "immunologically privileged" is used to denote a state where the recipient's immune system does not recognize the cells as foreign. Thus, only autologous transplants are possible in most cases when adult stem cells are used. Most presently envisioned forms of stem cell therapy are essentially customized medical procedures and therefore economic factors associated with such procedures limit their wide ranging potential.

The restoration of expression of at least some measured embryonic-specific genes has been observed in somatic cells following fusion with embryonic stem cells. However, the resulting cells are hybrids, often with a tetraploid genotype, and therefore not suited as normal or histocompatible cells for transplant purposes.

The use of somatic cell nuclear transfer has been shown to adequately reprogram somatic cell nuclear content to adopt pluripotency, however, raises a set of concerns beyond the moral status. The stresses placed on both the egg cell and the introduced nucleus are enormous, leading to a high loss in resulting cells. Furthermore, the procedure has to be performed manually under a microscope, and therefore, somatic cell nuclear transfer is very resource intensive. In addition, not all of the donor cell's genetic information is transferred, as the donor cell's mitochondria that contain their own mitochondrial DNA are left behind. The resulting hybrid cells retain those mitochondrial structures which originally belonged to the egg. As a consequence, clones are not perfect copies of the donor of the nucleus.

A major step towards patient derived pluripotent cells was achieved by Takahashi et al. in 2006. It was shown that the overexpression of defined transcription factors (TFs) which are known to regulate and maintain stem cell pluripotency (Takahasi et al., 2006, Cell 126, 663-676; Schulz & Hoffmann, 2007, Epigenetics 2, 37-42) can induce a pluripotent state of murine somatic fibroblasts, termed induced pluripotent stem (iPS) cells. In this study the authors identified OCT3/4, SOX2, KLF4 and c-MYC as being required for iPS cell generation (Takahasi et al., 2006). In a subsequent study the authors showed that the same TFs are able to reprogram adult human fibroblasts (Takahasi et al., 2007, Cell 131, 861-872), while others attributed this activity to a modified TF-cocktail composed of OCT3/4, SOX2, NANOG and LIN28 regarding human (Yu et al., 2007, Science Express) or murine fibroblasts (Wernig et al., 2007, Nature 448, 318-324). For those initial studies as well as most subsequent studies the reprogramming TFs were overexpressed using retro- or lentiviral vectors. Due to the silencing of viral promoters these studies reproducibly show that the expression exogenous TFs is shut down during the reprogramming process (reviewed by Hotta & Ellis, 2008, J. Cell Biochem. 105, 940-948). Accordingly, the pluripotent state is maintained by activated endogenous transcription factors. Furthermore, the silencing of the virally expressed TFs is prerequisite for the subsequent re-differentiation of iPS cells to tissue specific precursors (Yu et al., 2007). A major disadvantage of viral delivery is the stochastic reactivation of integrated retroviruses encoding potent oncogenes, which in the case of c-MYC led to the induction of tumors in chimeric mice (Okita et al., 2007, Nature 448, 313-317). Meanwhile it has been demonstrated that the generation of iPS cells is possible in absence of MYC (Nakagawa et al., 2008). Overall, only OCT4 and SOX2 have been reported being essential for the reprogramming, oncogenes like MYC and KLF4 seem to acts like enhancers (McDevitt & Palecek, 2008, Curr. Opin. Biotechnol. 19, 527-33). Accordingly it has been shown that other transforming gene products like SV40 Large-T antigen or hTERT can improve the efficiency of iPS generation (Mali et al., 2008, Stem Cells 26, 1998-2005). As the epigenetic reprogramming involves chromatin remodelling the addition of histone deacetylase (HDAC) inhibitors (like valproic acid) or DNA methyltransferase inhibitors (like 5'-azaC) greatly improve the reprogramming efficiency (Huangfu et al., 2008, Nat. Biotechnol. 26, 795-797) and reduced the need for TFs to OCT4 and SOX2 (Huangfu et al., 2008, Nat. Biotechnol. 26, 1269-1275).

Another strategy to reduce the risk associated with retroviral intergration into the host genome is the use of non-integrating adenoviral vectors, which mediate a transient transgene expression sufficient for reprogramming (Stadtfeld et al., 2008, Sciencexpress). Transgene integration is also avoided by the use of conventional eukaryotic expression plasmids leading to transient gene expression. So far, with this strategy MEFs have been successfully reprogrammed to iPS cells (Okita et al., 2008, Science 322, 949-53). Genomic integration has not been detected in this study, however, stable genomic integration in a small fraction of the cells of transfected plasmid DNA cannot be completely excluded.

Adult human fibroblasts are easily derived from healthy donors or—in future clinical applications—from patients without risky surgical intervention. However, a recent study has shown that human keratinocytes are more easily and more efficiently reprogrammend to iPS cells, and that e.g. hair follicle derived keratinocytes might be the better source of choice for patient derived iPS cells (Aasen et al., 2008, Nature Biotechnology).

There remains a need for improved technologies for reprogramming differentiated somatic cells to produce reprogrammed cells suitable for research, testing for quality control, and for use in cell therapy in high number and with good quality.

The present invention provides technologies of producing reprogrammed cells avoiding the use of DNA. These technologies use cells that are easily and inexpensively obtained in unlimited quantities and provide reprogrammed cells useful in cell therapy. The approach according to the present invention completely lacks the risk of genomic integration and opens the possibility of reprogramming without modification of the host genome.

SUMMARY OF THE INVENTION

The present invention exploits the fact that, when provided with appropriate factors, a terminally differentiated cell's fate can be redirected to pluripotentiality. Specifically, the present invention provides technology for reprogramming an animal differentiated somatic cell to a cell having stem cell properties. This method allows de-differentiation of one type of somatic cells into pluripotent stem-like cells using a defined system in vitro. The method of the invention in one embodiment provides autologous (isogeneic) cell types for cell transplantation in the same individual that donated the initial somatic cell sample.

According to the present invention, one or more somatic cells are provided with RNA capable of expressing one or more factors that induce the reprogramming of somatic cells to cells having stem cell characteristics. Expression of RNA capable of expressing these factors confers characteristics of an undifferentiated cell to a somatic cell and facilitates reprogramming of the somatic cell.

Introduction of the factors in the form of RNA has the advantage, relative to the use of DNA constructs, that, for expression, RNA need only get into the cytoplasm of the cells, not into the cell nucleus. Therefore RNA transfer is not dependent on the division activity of the cells to be transfected. Furthermore, the transfection rates attainable with RNA are relatively high, for many cell types even >90%, and therefore, there is no need for selection. The amounts of protein achieved correspond to those in physiological expression.

Furthermore, according to the invention, it is possible to control the amount of RNA that is introduced into a cell as well as the stability and translation level of the RNA in the cell.

Hence the amount and time of expression of certain factors expressed by the RNA in the cell can be adjusted as necessary. In this way it is possible to simulate the effects of different levels of expression in a cell and introduce RNA into a cell in amounts sufficient to induce reprogramming and de-differentiation of somatic cells to produce cells having stem cell characteristics, preferably in amounts sufficient to allow development of somatic cells into pluripotent cells.

Most importantly, transfected RNA does not result in significant integration into the host genome. In contrast, transfection of DNA for medical use is considered as gene therapy. DNA transfer is associated with a significant risk of mutations in the host genome with the increased risk of malignant transformation. Thus, RNA transfer has a much better safety profile and is not regarded as gene therapy. Moreover, transfected RNA is degraded in the host cell within days. This means that a stem cell induced by transfection of RNA is genetically identical to an autologous natural stem cell. Thus, cell types and tissues obtained from such stem cells are genetically non-discriminable from their autologous natural counterparts. In contrast, a stem cell induced by DNA transfection carries additional foreign genes. All tissues which derive from such a recombinant stem cell carry the same genetic markers and thus, exhibit an increased risk of malignant transformation.

In one aspect, the present invention relates to a method for producing cells having stem cell characteristics comprising the steps of (i) providing a cell population comprising somatic cells, (ii) introducing RNA into at least a portion of said somatic cells said RNA when introduced into a somatic cell is capable of inducing the development of stem cell characteristics, and (iii) allowing the development of cells having stem cell characteristics. In one embodiment, the RNA is derived from an undifferentiated cell such as a stem cell, for example an embryonic stem cell or an adult stem cell. In this respect, the term "derived" denotes for the fact that the RNA either has been obtained from the cell, e.g. by isolation and optionally fractionation, and thus, is an isolate of cellular RNA or a fraction thereof and/or has a composition similar to the RNA composition of the cell from which it is derived, or a fraction thereof. In one embodiment, the RNA comprises whole-cell RNA. In another embodiment, the RNA is specific for said undifferentiated cell. In this embodiment, the RNA may be a fraction of whole-cell RNA. In one embodiment, the RNA has been obtained by in vitro transcription.

Preferably, step (iii) comprises culturing the somatic cells under embryonic stem cell culture conditions, preferably conditions suitable for maintaining pluripotent stem cells in an undifferentiated state.

According to the present invention, the RNA preferably is introduced into said at least a portion of somatic cells by electroporation.

In one embodiment of the method of the invention, the stem cell characteristics comprise an embryonic stem cell morphology, wherein said embryonic stem cell morphology preferably comprises morphological criteria selected from the group consisting of compact colonies, high nucleus to cytoplasm ratio and prominent nucleoli. In certain embodiments, the cells having stem cell characteristics have normal karyotypes, express telomerase activity, express cell surface markers that are characteristic for embryonic stem cells and/or express genes that are characteristic for embryonic stem cells. The cell surface markers that are characteristic for embryonic stem cells may be selected from the group consisting of stage-specific embryonic antigen-3 (SSEA-3), SSEA-4, tumor-related antigen-1-60 (TRA-1-60), TRA-1-81, and TRA-2-49/6E and the genes that are characteristic for embryonic stem cells may be selected from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT).

Preferably, the cells having stem cell characteristics are de-differentiated and/or reprogrammed somatic cells. Preferably, the cells having stem cell characteristics exhibit the essential characteristics of embryonic stem cells such as a pluripotent state. Preferably, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into neuronal cells and/or cardiac cells.

In one embodiment, the somatic cells are embryonic stem cell derived somatic cells with a mesenchymal phenotype. In a preferred embodiment, the somatic cells are fibroblasts such as fetal fibroblasts or postnatal fibroblasts or keratinocytes, preferably hair follicle derived keratinocytes. In further embodiments, the fibroblasts are lung fibroblasts, foreskin fibroblasts or dermal fibroblasts. In particular embodiments, the fibroblasts are fibroblasts as deposited at the American Type Culture Collection (ATCC) under Catalog No. CCL-186 or as deposited at the American Type Culture Collection (ATCC) under Catalog No. CRL-2097. In one embodiment, the fibroblasts are adult human dermal fibroblast. Preferably, the somatic cells are human cells. According to the present invention, the somatic cells may be genetically modified.

In a further aspect, the present invention relates to a method for producing cells having stem cell characteristics comprising the steps of (i) providing a cell population comprising somatic cells, (ii) introducing RNA capable of expressing OCT4 and RNA capable of expressing SOX2 into at least a portion of said somatic cells and (iii) allowing the development of cells having stem cell characteristics. In one embodiment, the method further comprises introducing RNA capable of expressing NANOG and/or RNA capable of expressing LIN28 and, alternatively or additionally, further comprises introducing RNA capable of expressing KLF4 and/or RNA capable of expressing c-MYC.

In one embodiment, step (ii) comprises introducing RNA capable of expressing OCT4, RNA capable of expressing SOX2, RNA capable of expressing NANOG and RNA capable of expressing LIN28 into at least a portion of said somatic cells.

In another embodiment, step (ii) comprises introducing RNA capable of expressing OCT4, RNA capable of expressing SOX2, RNA capable of expressing KLF4 and RNA capable of expressing c-MYC into at least a portion of said somatic cells.

Preferably, step (iii) comprises culturing the somatic cells under embryonic stem cell culture conditions, preferably conditions suitable for maintaining pluripotent stem cells in an undifferentiated state.

According to the present invention, the RNA preferably is introduced into said at least a portion of somatic cells by electroporation.

In one embodiment of the method of the invention, the stem cell characteristics comprise an embryonic stem cell morphology, wherein said embryonic stem cell morphology preferably comprises morphological criteria selected from the group consisting of compact colonies, high nucleus to cytoplasm ratio and prominent nucleoli. In certain embodiments, the cells having stem cell characteristics have normal karyotypes, express telomerase activity, express cell surface markers that are characteristic for embryonic stem cells and/or express genes that are characteristic for embryonic stem cells. The cell surface markers that are characteristic for embryonic stem cells may be selected from the group consisting of stage-specific embryonic antigen-3 (SSEA-3), SSEA-4, tumor-related antigen-1-60 (TRA-1-60), TRA-1-81, and TRA-2-49/6E and the genes that are characteristic for embryonic stem cells may be selected from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT).

Preferably, the cells having stem cell characteristics are de-differentiated and/or reprogrammed somatic cells. Preferably, the cells having stem cell characteristics exhibit the essential characteristics of embryonic stem cells such as a pluripotent state. Preferably, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into neuronal cells and/or cardiac cells.

In one embodiment, the somatic cells are embryonic stem cell derived somatic cells with a mesenchymal phenotype. In a preferred embodiment, the somatic cells are fibroblasts such as fetal fibroblasts or postnatal fibroblasts or keratinocytes, preferably hair follicle derived keratinocytes. In further embodiments, the fibroblasts are lung fibroblasts, foreskin fibroblasts or dermal fibroblasts. In particular embodiments, the fibroblasts are fibroblasts as deposited at the American Type Culture Collection (ATCC) under Catalog No. CCL-186 or as deposited at the American Type Culture Collection (ATCC) under Catalog No. CRL-2097. In one embodiment, the fibroblasts are adult human dermal fibroblast. Preferably, the somatic cells are human cells. According to the present invention, the somatic cells may be genetically modified.

In a further aspect, the present invention relates to a method for reprogramming an animal differentiated somatic cell to a cell having stem cell properties, comprising the step of introducing RNA capable of expressing one or more factors allowing the reprogramming of said somatic cell to a cell having stem cell characteristics into said somatic cell.

In one embodiment, the RNA is derived from an undifferentiated cell such as a stem cell, for example an embryonic stem cell or an adult stem cell. In one embodiment, the RNA comprises whole-cell RNA. In another embodiment, the RNA is specific for said undifferentiated cell. In this embodiment, the RNA may be a fraction of whole-cell RNA. In one embodiment, the RNA has been obtained by in vitro transcription. In different embodiments, said one or more factors capable of being expressed by the RNA comprise an assembly of factors selected from the group consisting of (i) OCT4 and SOX2, (ii) OCT4, SOX2, and one or both of NANOG and LIN28, (iii) OCT4, SOX2 and one or both of KLF4 and c-MYC. In one embodiment, said one or more factors capable of being expressed by the RNA comprise OCT4, SOX2, NANOG and LIN28 or OCT4, SOX2, KLF4 and c-MYC. Preferably, the RNA is introduced into said animal differentiated somatic cell by electroporation or microinjection. Preferably, the method further comprises allowing the development of cells having stem cell characteristics, e.g. by culturing the somatic cell under embryonic stem cell culture conditions, preferably conditions suitable for maintaining pluripotent stem cells in an undifferentiated state.

In one embodiment of the method of the invention, the stem cell characteristics comprise an embryonic stem cell morphology, wherein said embryonic stem cell morphology preferably comprises morphological criteria selected from the group consisting of compact colonies, high nucleus to cytoplasm ratio and prominent nucleoli. In certain embodiments, the cell having stem cell characteristics has a normal karyotype, expresses telomerase activity, expresses cell surface markers that are characteristic for embryonic stem cells and/or expresses genes that are characteristic for embryonic stem cells. The cell surface markers that are characteristic for embryonic stem cells may be selected from the group consisting of stage-specific embryonic antigen-3 (SSEA-3), SSEA-4, tumor-related antigen-1-60 (TRA-1-60), TRA-1-81, and TRA-2-49/6E and the genes that are characteristic for embryonic stem cells may be selected from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT).

Preferably, the cell having stem cell characteristics is a de-differentiated and/or reprogrammed somatic cell. Preferably, the cell having stem cell characteristics exhibits the essential characteristics of embryonic stem cells such as a pluripotent state. Preferably, the cell having stem cell characteristics has the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cell having stem cell characteristics has the developmental potential to differentiate into neuronal cells and/or cardiac cells.

In one embodiment, the animal differentiated somatic cell is an embryonic stem cell derived somatic cell with a mesenchymal phenotype. In a preferred embodiment, the somatic cell is a fibroblast such as fetal fibroblast or postnatal fibroblast or a keratinocyte, preferably hair follicle derived keratinocyte. In further embodiments, the fibroblast is a lung fibroblast, foreskin fibroblast or dermal fibroblast. In particular embodiments, the fibroblast is a fibroblast as deposited at the American Type Culture Collection (ATCC) under Catalog No. CCL-186 or as deposited at the American Type Culture Collection (ATCC) under Catalog No. CRL-2097. In one embodiment, the fibroblast is an adult human dermal fibroblast. Preferably, the animal differentiated somatic cell is a human cell. According to the present invention, the animal differentiated somatic cell may be genetically modified.

Particular embodiments of the methods of the present invention further comprise the step of cryopreserving the cells having stem cell characteristics.

In further aspects, the present invention relates to cells having stem cell characteristics prepared by the methods of the present invention and a composition of cells having stem cell characteristics prepared by the methods of the present invention. In one embodiment, the composition is a pharmaceutical composition.

In further aspects, the present invention relates to the use of the cells or the composition of the present invention in medicine, in particular in transplantation medicine, for producing a disease model or for drug development.

In a further aspect, the present invention relates to a method of deriving differentiated cell types comprising the step of culturing the cells having stem cell characteristics of the present invention or the composition of cells having stem cell characteristics of the present invention under conditions that induce or direct partial or complete differentiation to a particular cell type. In one embodiment, the conditions that induce or direct partial or complete differentiation to a particular cell type comprise the presence of at least one differentiation factor. Preferably, the somatic cell type of the differentiated cells obtained according to the present invention is different from the somatic cell type of the somatic cells used for de-differentiation. Preferably, the de-differentiated cells are derived from fibroblastic cells and said re-differentiated cell types are different from fibroblastic cells. In another embodiment, the de-differentiated cells are derived from keratinocytes and said re-differentiated cell types are different from keratinocytes.

In a further aspect, the present invention relates to an assay to identify one or more factors useful for reprogramming an animal differentiated somatic cell to a cell having stem cell characteristics comprising the steps of introducing RNA capable of expressing one or more factors into said somatic cell and determining whether said somatic cell has developed into a cell having stem cell characteristics. Preferably, the method further comprises the step of allowing the development of cells having stem cell characteristics, e.g. by culturing the animal differentiated somatic cell under embryonic stem cell culture conditions, preferably conditions suitable for maintaining pluripotent stem cells in an undifferentiated state. Preferably, the RNA is introduced into said animal differentiated somatic cell by electroporation or microinjection.

In one embodiment, the step of determining whether said somatic cell has developed into a cell having stem cell characteristics comprises comparing the gene expression of the cell obtained by the method of the present invention with gene expression found in embryonic stem cells, preferably of the same cell type, to determine whether said one or more factors play a role in cellular reprogramming.

In one embodiment, the step of introducing RNA capable of expressing one or more factors into said somatic cell comprises introducing RNA capable of expressing factors known to be involved in reprogramming an animal differentiated somatic cell to a cell having stem cell characteristics. In one embodiment, said factors known to be involved in reprogramming an animal differentiated somatic cell to a cell having stem cell characteristics include at least one factor selected from the group consisting of OCT4, SOX2, NANOG, LIN28, KLF4 and c-MYC. In one embodiment, said factors known to be involved in reprogramming an animal differentiated somatic cell to a cell having stem cell characteristics include a combination of OCT4 and SOX2, a combination of OCT4, SOX2, NANOG and/or LIN28 and a combination of OCT4, SOX2, KLF4 and/or c-MYC.

Various embodiments of the somatic cell, the cell having stem cell characteristics and the culture conditions for allowing the development of cells having stem cell characteristics are as described above for the methods according to the other aspects of the present invention.

In a further aspect, the present invention relates to a kit for producing cells having stem cell characteristics comprising RNA capable of expressing one or more factors known to be involved in reprogramming an animal differentiated somatic cell to a cell having stem cell characteristics. Preferably, said kit comprises RNA capable of expressing OCT4 and RNA capable of expressing SOX2 and preferably further comprises (i) RNA capable of expressing NANOG and/or RNA capable of expressing LIN28 and/or (ii) RNA capable of expressing KLF4 and/or RNA capable of expressing c-MYC. The kit may further comprise an embryonic stem cell culture medium.

In even a further aspect, the present invention relates to a pharmaceutical composition comprising RNA which when introduced into a somatic cell is capable of inducing the development of stem cell characteristics in said cell. Particular embodiments of the RNA, the somatic cell and the cell having stem cell characteristics are as described herein for the other aspects of the invention.

BRIEF DESCRIPTION OF THE DRAWINGS

FIG. 2A: Comparison of the duplicates of cells transfected with SYT-SSX2 or eGFP;

FIG. 2B: Representation of replicates after 24 h.

FIG. 3A: Scatter blot of all analyzed genes. Comparison of SYT-SSX2-transfected cells with eGFP-transfected cells following transfection of each 15 μg IVT RNA. Representation of replicates after 24 h. Yellow-orange shows differential expression in the non-significant region, i.e. below a factor of two, red and green show up- and downregulation, respectively, by a factor greater than two.

FIG. 3B: Representation of the number of genes which are significantly regulated after 8 h and 24 h, respectively, by transfection of 15 μg IVT RNA of the respective gene.

FIGS. 4A1-4A3 and 4B: Overview of different 5'-CAP-structures.

FIGS. 4A1-4A3: Pictured are the natural 5'CAP-structure of mRNA and chemical modified versions of this 5'-CAP (ARCA, D1 and D2-D1 and D2 refer to the two diastereoisomers produced by the phosphorothioate moiety), which were shown to stabilize mRNA.

FIG. 4B: Schematic overview of in vitro translated mRNA (IVT-RNA) synthesis.

CCD1079Sk fibroblasts and MEFs were electroporated once with 10 μg IVT-RNA encoding eGFP. Voltage and capacity were chosen as indicated. 24 h post electroporation the transfection efficiencies [%] were measured by FACS, mean fluorescence levels are given in parenthesis.

Figure 6:
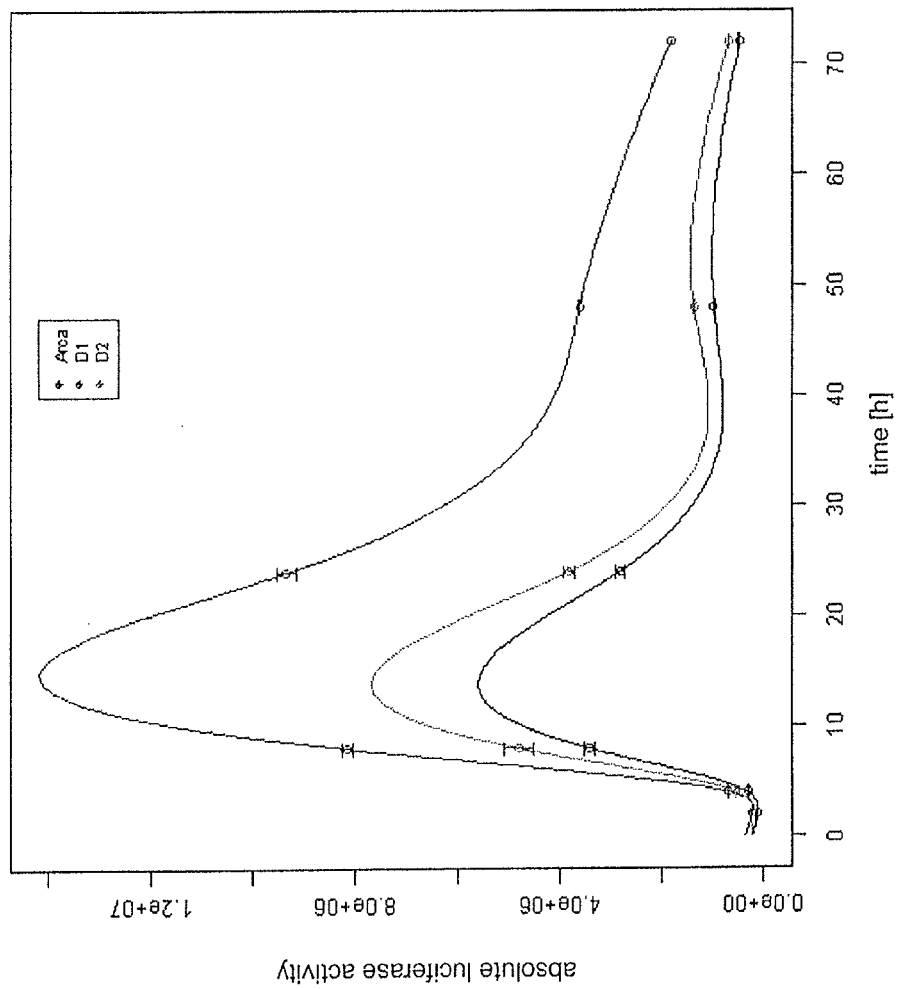

FIG. 6: IVT RNA cap structure optimization.

CCD1079Sk fibroblasts were electroporated (250V, 300 μF) either with IVT-RNA of ARCA-luc (encoding Luciferase (luc) with ARCA-5'-CAP), D1-luc or D2-luc (each 10 μg). After 2 h, 4 h, 8 h, 24 h, 48 h, and 72 h luciferase assays were performed in duplicates. Data are expressed as mean luciferase activity ±SD.

Figure 7:
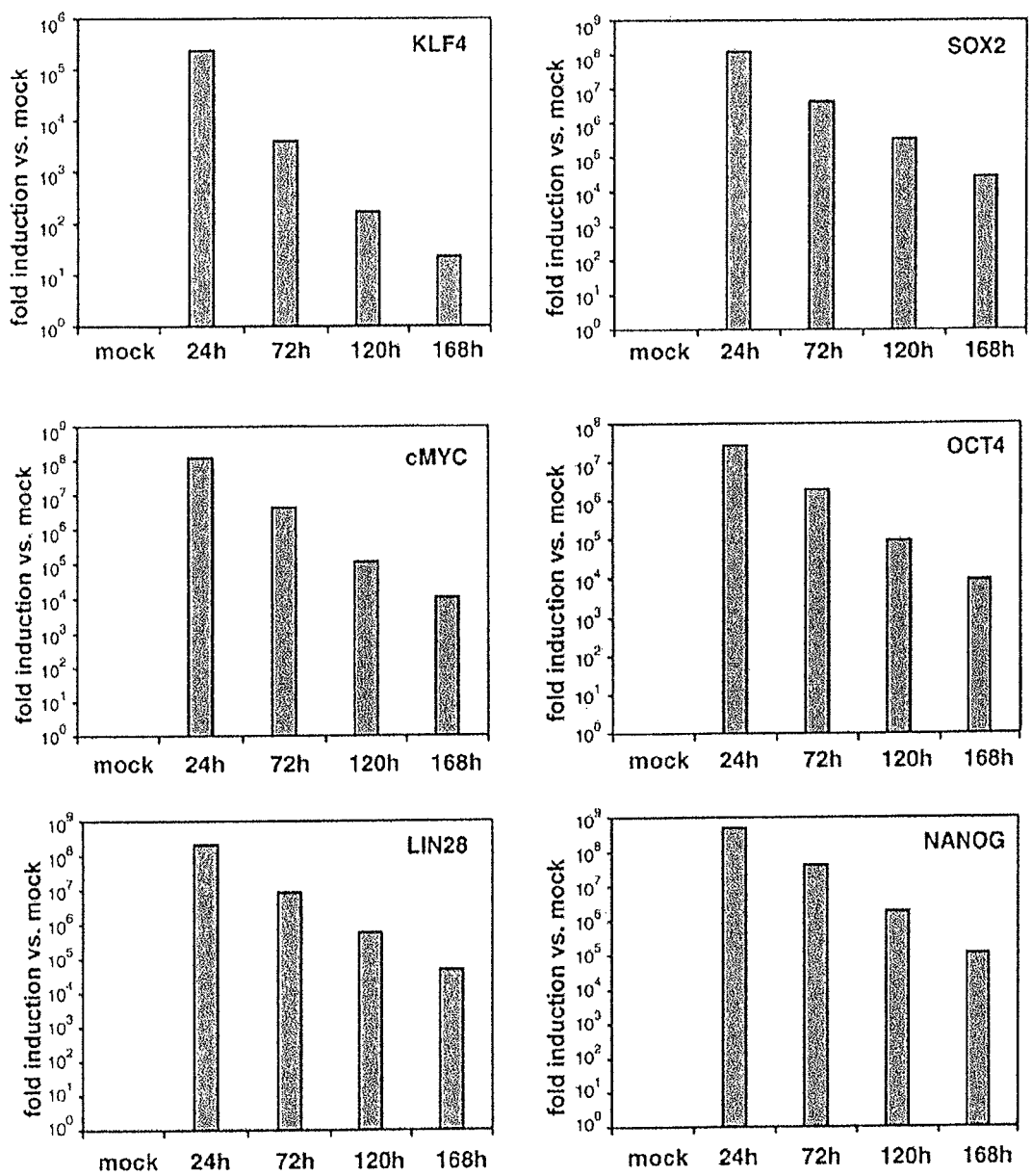

FIG. 7: Persistence of electroporated IVT-RNA in human fibroblasts.

CCD1079Sk fibroblasts were electroporated once with 15 μg IVT-RNA of each transcription factor. The intracellular levels of these IVT-RNA constructs were quantified by qRT-PCR 7 days post electroporation.

Figure 8A:
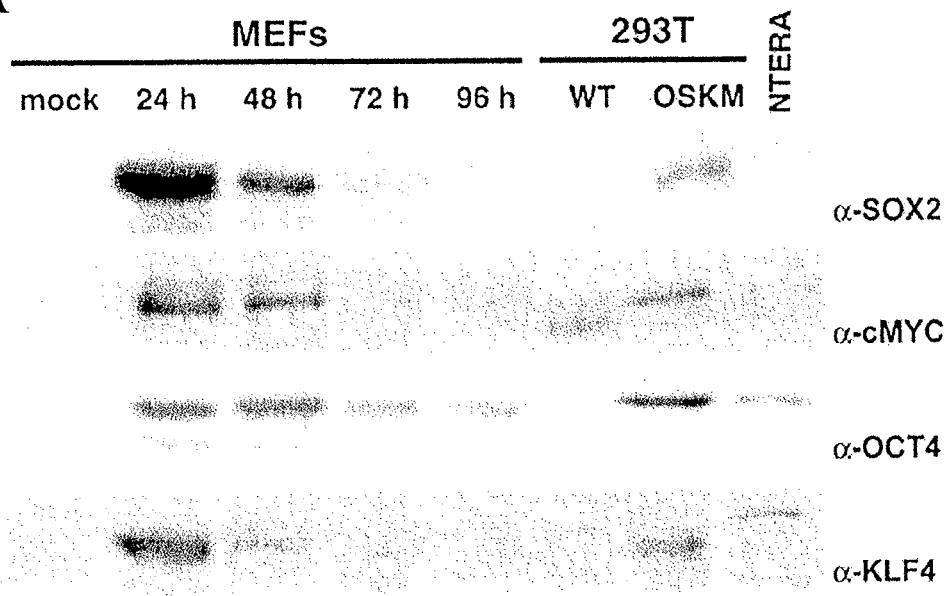
Figure 8B:
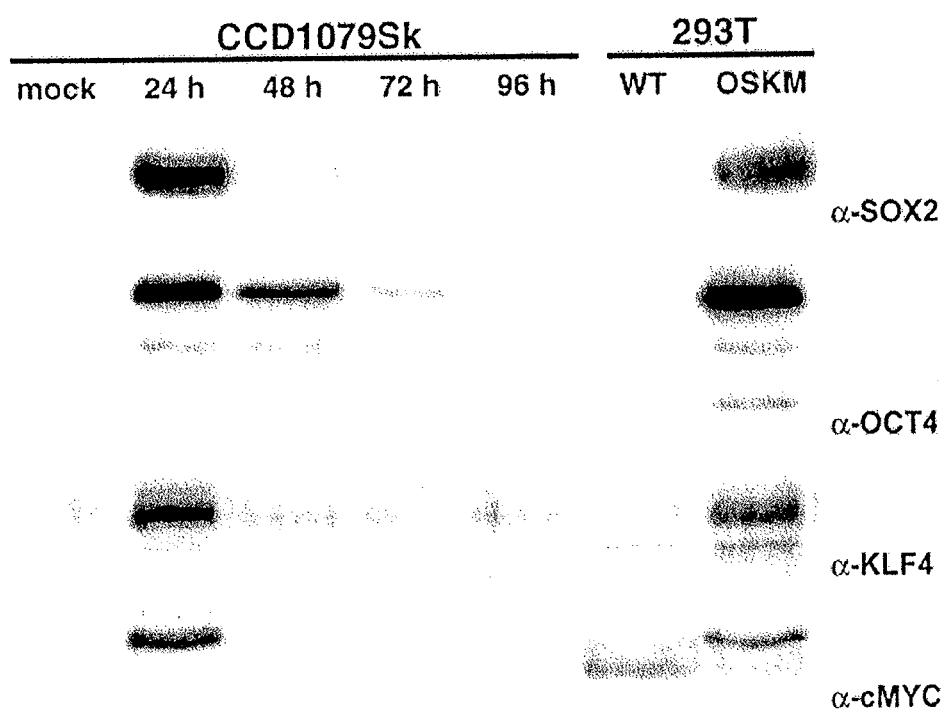

FIGS. 8A and 8B: Expression of human and murine transcription factors after electroporation of IVT-RNA constructs.

MEFs (FIG. 8A) and CCD1079Sk fibroblasts (FIG. 8B) were electroporated once with respectively 10 μg or 2.5 μg IVT-RNA encoding the four transcription factors (TFs)

OCT4, SOX2, KLF4 and c-MYC (OSKM). Cells were lysed at the indicated timepoints post electroporation. The protein expression was monitored by Western Bloting using specific antibodies. 293T-cells electroporated with µg IVT-RNA encoding OSKM were used as positive control.

Figure 9A:
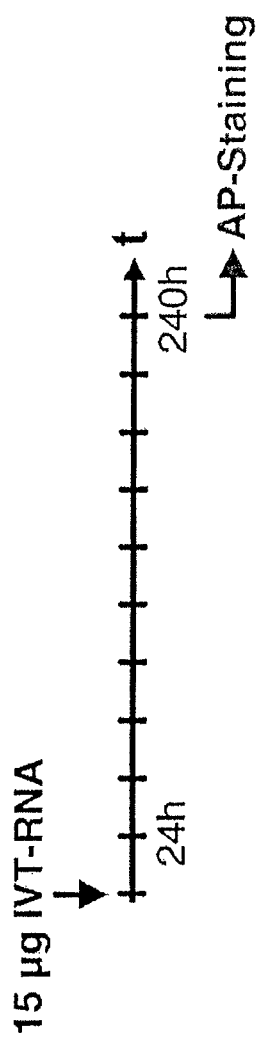
Figure 9B:
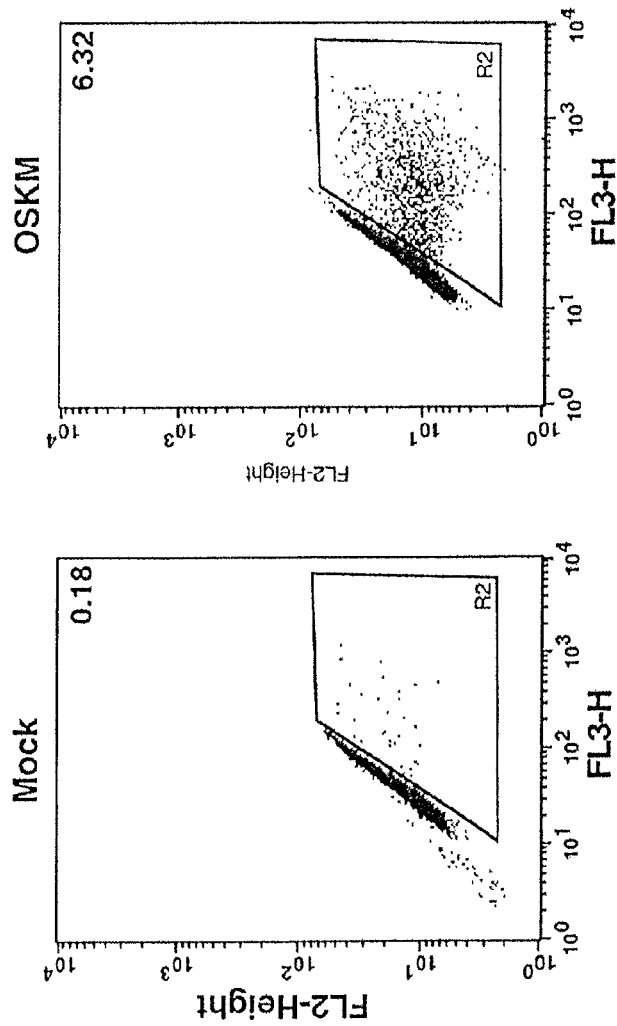

FIGS. 9A and 9B: Alkaline phosphatase staining of electroporated human CCD1079Sk fibroblasts.

FIG. 9A: CCD1079Sk fibroblasts were electroporated once either with IVT-RNA encoding the four TFs OSKM or with buffer (mock) and cultivated in human ES cell medium.

FIG. 9B: After 10 days cells were stained for alkaline phosphatase (AP) and the resulting red fluorescence was monitored by FACS.

Figures 10A, 10B:
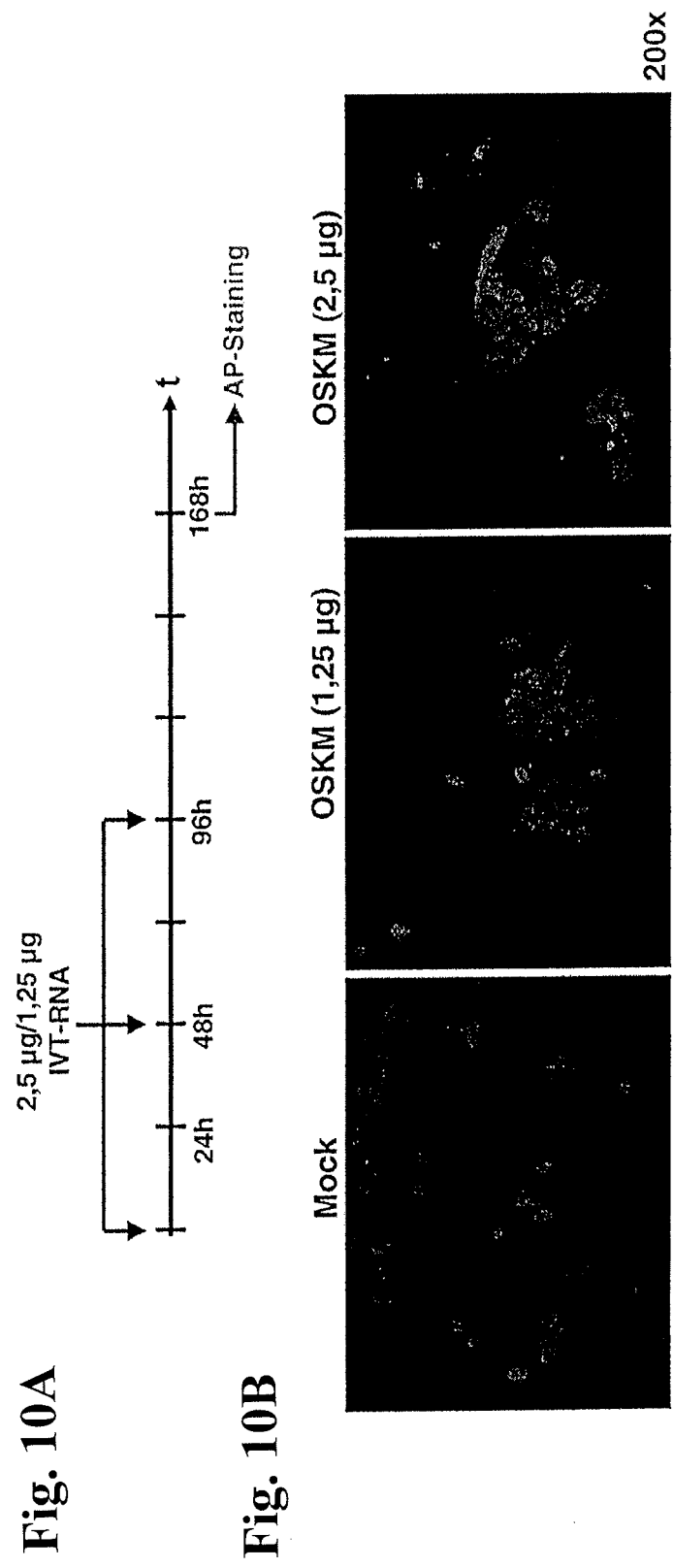

FIGS. 10A and 10B: Alkaline phosphatase staining of electroporated human CCD1079Sk fibroblasts.

FIG. 10A: CCD1079Sk cells were electroporated three consecutive times in 48 h intervals with IVT-RNA encoding either GFP (mock) or the four TFs OSKM (2.5 or 1.25 µg each). OSKM or mock transfected cells were cultivated in iPS medium.

FIG. 10B: After 192 h cells were stained for alkaline phosphatase (AP) and monitored by fluorescence microscopy.

Figures 11A, 11B:
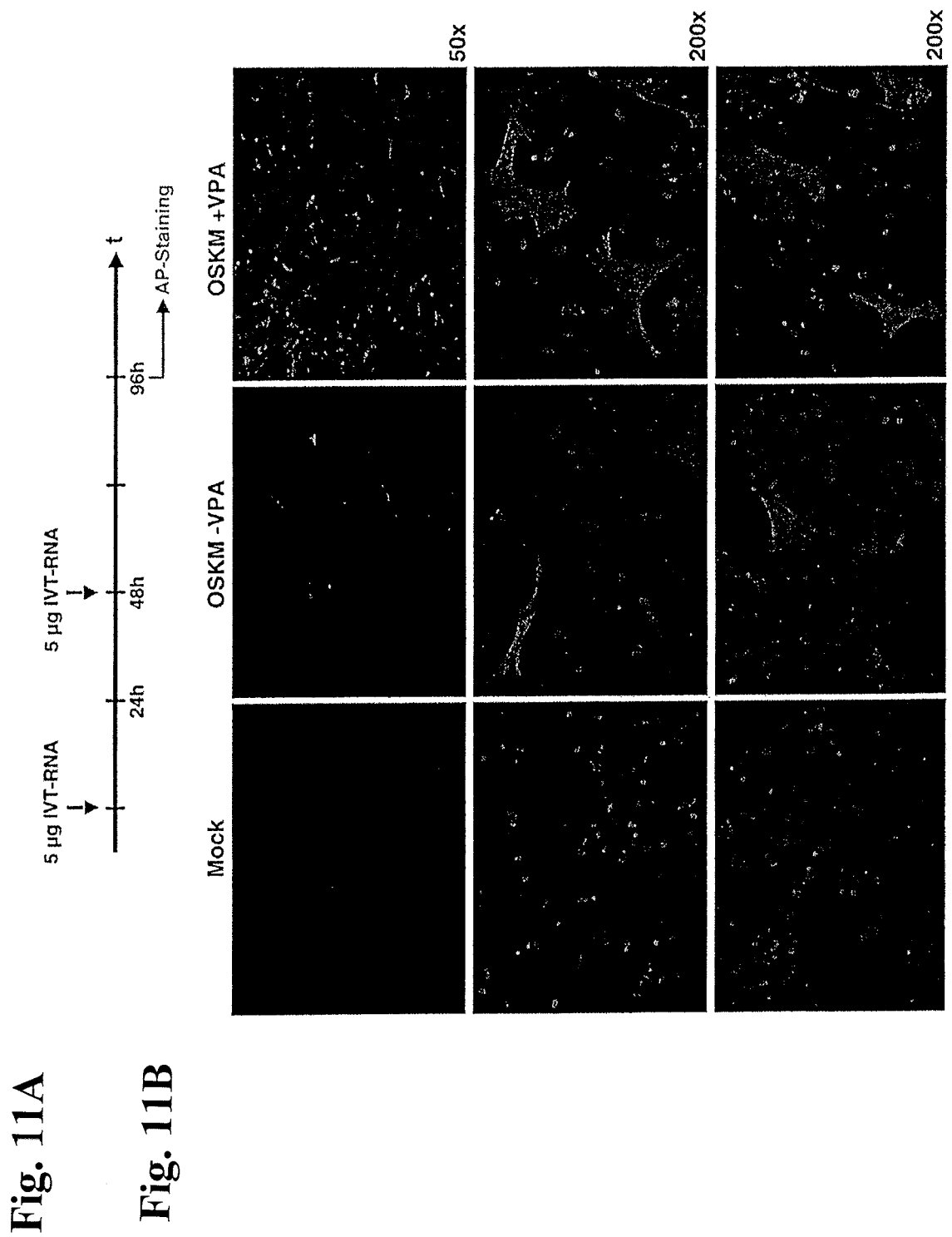

FIGS. 11A and 11B: Alkaline phosphatase staining of electroporated MEFs.

FIG. 11A: MEFs cultivated until passage 3 were electroporated in 48 h intervals with IVT-RNA encoding either GFP (mock) or the four murine TFs OSKM (5 µg each). OSKM or mock transfected MEFs were cultivated in mouse ES cell medium in the presence or absence of 2 mM valproic acid (VPA) as indicated.

FIG. 11B: After 96 h cells were stained for alkaline phosphatase (AP) and monitored by fluorescence microscopy.

Figure 12A:
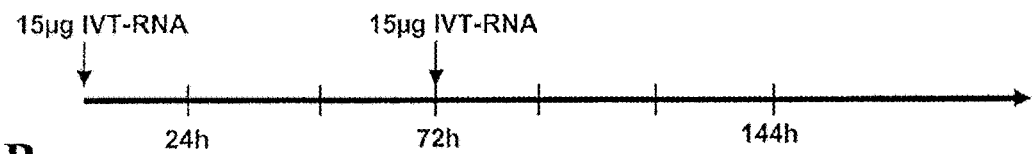
Figure 12B:
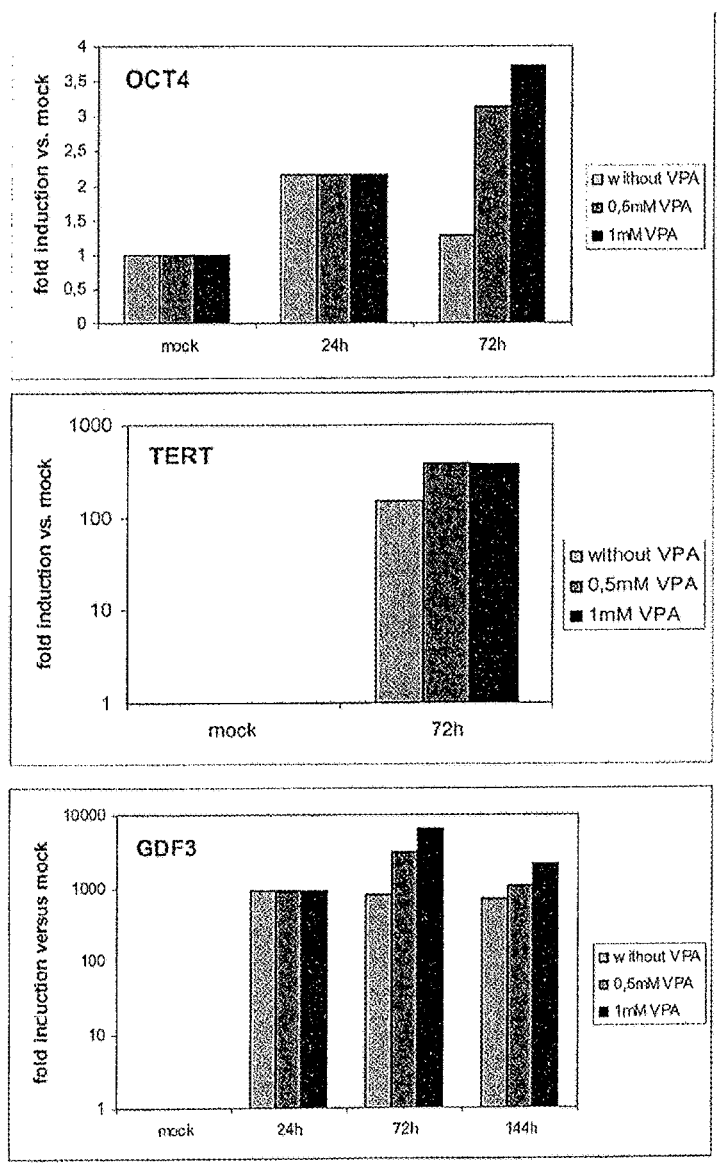

FIGS. 12A and 12B: Expression of human ES-marker genes of electroporated CCD1079Sk cells.

FIG. 12A: CCD1079Sk fibroblasts were electroporated two times either with buffer (mock) or with 15 µg IVT-RNA encoding the transcription factors OSKM and cultivated in human ES cell medium in the presence or absence of VPA (0.5 or 1 mM) as indicated.

FIG. 12B: After the indicated time points, 10% of the cells were removed from the cultures prior to subsequent electroporation, total RNA was isolated and mRNA-expression of the human ES-marker genes OCT4 (endogenous), TERT and GDF3 was evaluated by real-time PCR.

Figure 13A:
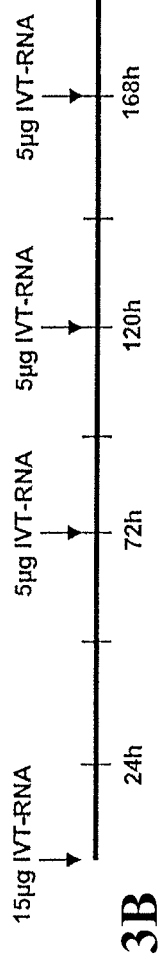
Figure 13B:
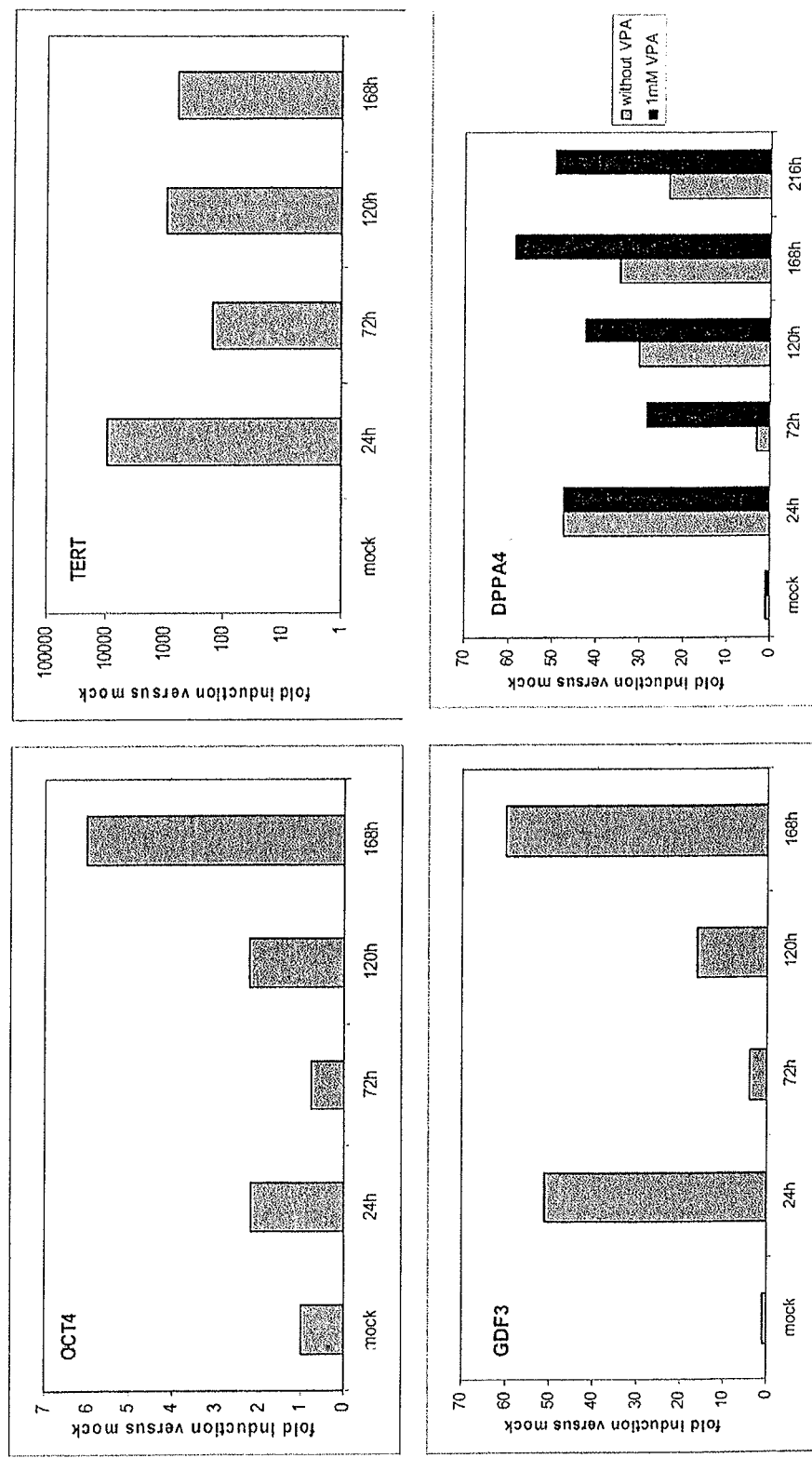

FIGS. 13A and 13B: Expression of human ES-marker genes of electroporated CCD1079Sk cells.

FIG. 13A: CCD1079Sk fibroblasts were electroporated as indicated either with 15 µg or 5 µg IVT-RNA encoding the transcription factors OSKM or with buffer (mock) and cultivated in human ES cell medium in the presence or absence of 1 mM VPA as indicated.

FIG. 13B: After the indicated time points, 10% of the cells were removed from the cultures prior to subsequent electroporation, total RNA was isolated and mRNA-expression of the human ES-marker genes OCT4 (endogenous), TERT, GDF3 and DPPA4 was quantified by qRT-PCR.

Figure 14A:
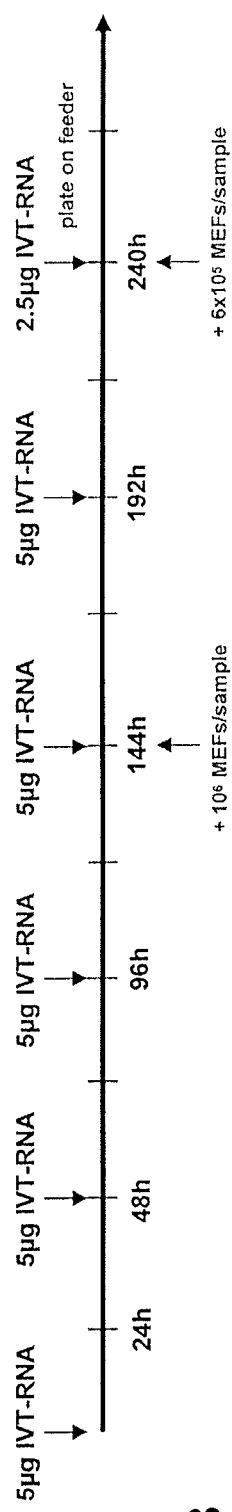
Figure 14B:

FIGS. 14A and 14B: Expression of human ES-marker genes of electroporated CCD1079Sk cells.

FIG. 14A: MEFs were electroporated six consecutive times with 5 or 2.5 µg IVT-RNA encoding either GFP (mock) or the four murine transcription factors OSKM and cultivated in mouse ES cell medium in the presence or absence of 2 mM VPA as indicated.

FIG. 14B: After the indicated time points, 10% of the cells were removed from the cultures prior to subsequent electroporation, total RNA was isolated and mRNA-expression of the murine ES-marker gene mTert was evaluated by qRT-PCR.

DETAILED DESCRIPTION OF THE INVENTION

The present invention provides technology to change one type of highly specialized somatic cells, e.g. fibroblasts or keratinocytes, into another type, e.g., neuronal cells, via a pluripotent cell intermediate.

Specifically, by providing a differentiated somatic cell with factors present in pluripotent cell types, preferably stem cells, more preferably embryonic stem cells, the invention restores the cell's epigenetic memory to a state similar to that of pluripotent stem cells. With the present invention, embryos do not have to be used, created, or destroyed to generate cells having stem cell characteristics, in particular pluripotency, thus eliminating ethical concerns. Furthermore, the present invention does not require the use of vectors that integrate into the genome such as viral vectors potentially introducing mutations at the insertion site.

The somatic cells used according to the present invention have an important advantage over oocytes as a means of inducing reprogramming in that they can be easily expanded in number in vitro. In addition, the present invention allows the use of patient-specific somatic cells and thus, largely eliminates the concerns of immune rejection and problems associated with patient immunosuppression. Using cells generated according to the present invention for autologous cell transplantation is unlikely to induce adverse side effects and/or resistance. If required, repeated cell transplantation is feasible. However, since the present invention will significantly reduce the need for immunosuppression of the patient to reduce acute and hyperacute rejection the need for repeated transplantation procedures will also be alleviated, reducing the cost of disease treatment.

Terms such as "cell having stem cell characteristics", "cell having stem cell properties" or "stem like cell" are used herein to designate cells which, although they are derived from differentiated somatic non-stem cells, exhibit one or more features typical for stem cells, in particular embryonic stem cells. Such features include an embryonic stem cell morphology such as compact colonies, high nucleus to cytoplasm ratio and prominent nucleoli, normal karyotypes, expression of telomerase activity, expression of cell surface markers that are characteristic for embryonic stem cells, and/or expression of genes that are characteristic for embryonic stem cells. The cell surface markers that are characteristic for embryonic stem cells are, for example, selected from the group consisting of stage-specific embryonic antigen-3 (SSEA-3), SSEA-4, tumor-related antigen-1-60 (TRA-1-60), TRA-1-81, and TRA-2-49/6E. The genes that are characteristic for embryonic stem cells are selected, for example, from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT). In one embodiment, the one or more features typical for stem cells include pluripotency.

A "stem cell" is a cell with the ability to self-renew, to remain undifferentiated, and to become differentiated. A stem cell can divide without limit, for at least the lifetime of the animal in which it naturally resides. A stem cell is not terminally differentiated; it is not at the end stage of a differentiation pathway. When a stem cell divides, each daughter cell can either remain a stem cell or embark on a course that leads toward terminal differentiation.

Totipotent stem cells are cells having totipotential differentiation properties and being capable of developing into a complete organism. This property is possessed by cells up to the 8-cell stage after fertilization of the oocyte by the sperm. When these cells are isolated and transplanted into the uterus, they can develop into a complete organism.

Pluripotent stem cells are cells capable of developing into various cells and tissues derived from the ectodermal, mesodermal and endodermal layers. Pluripotent stem cells which are derived from the inner cell mass located inside of blastocysts, generated 4-5 days after fertilization are called "embryonic stem cells" and can differentiate into various other tissue cells but cannot form new living organisms.

Multipotent stem cells are stem cells differentiating normally into only cell types specific to their tissue and organ of origin. Multipotent stem cells are involved not only in the growth and development of various tissues and organs during the fetal, neonatal and adult periods but also in the maintenance of adult tissue homeostasis and the function of inducing regeneration upon tissue damage. Tissue-specific multipotent cells are collectively called "adult stem cells".

An "embryonic stem cell" is a stem cell that is present in or isolated from an embryo. It can be pluripotent, having the capacity to differentiate into each and every cell present in the organism, or multipotent, with the ability to differentiate into more than one cell type.

As used herein, "embryo" refers to an animal in the early stages of it development. These stages are characterized by implantation and gastrulation, where the three germ layers are defined and established and by differentiation of the germs layers into the respective organs and organ systems. The three germ layers are the endoderm, ectoderm and mesoderm.

A "blastocyst" is an embryo at an early stage of development in which the fertilized ovum has undergone cleavage, and a spherical layer of cells surrounding a fluid-filled cavity is forming, or has formed. This spherical layer of cells is the trophectoderm. Inside the trophectoderm is a cluster of cells termed the inner cell mass (ICM). The trophectoderm is the precursor of the placenta, and the ICM is the precursor of the embryo.

An adult stem cell, also called a somatic stem cell, is a stem cell found in an adult. An adult stem cell is found in a differentiated tissue, can renew itself, and can differentiate, with some limitations, to yield specialized cell types of its tissue of origin. Examples include mesenchymal stem cells, hematopoietic stem cells, and neural stem cells.

A "differentiated cell" is a mature cell that has undergone progressive developmental changes to a more specialized form or function. Cell differentiation is the process a cell undergoes as it matures to an overtly specialized cell type. Differentiated cells have distinct characteristics, perform specific functions, and are less likely to divide than their less differentiated counterparts.

An "undifferentiated" cell, for example, an immature, embryonic, or primitive cell, typically has a nonspecific appearance, may perform multiple, non-specific activities, and may perform poorly, if at all, in functions typically performed by differentiated cells.

The term "autologous" is used to describe anything that is derived from an organism's own tissues, cells, or DNA. For example, "autologous transplant" refers to a transplant of tissue or organs derived from the same organism. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the organism.

"Somatic cell" refers to any and all differentiated cells and does not include stem cells, germ cells, or gametes. Preferably, "somatic cell" as used herein refers to a terminally differentiated cell.

As used herein, "committed" refers to cells which are considered to be permanently committed to a specific function. Committed cells are also referred to as "terminally differentiated cells".

As used herein, "differentiation" refers to the adaptation of cells for a particular form or function. In cells, differentiation leads to a more committed cell.

As used herein, "de-differentiation" refers to loss of specialization in form or function. In cells, de-differentiation leads to a less committed cell.

As used herein "reprogramming" refers to the resetting of the genetic program of a cell. A reprogrammed cell preferably exhibits pluripotency.

The terms "de-differentiated" and "reprogrammed" or similar terms are used interchangeably herein to denote somatic cell-derived cells having stem cell characteristics. However, said terms are not intended to limit the subject-matter disclosed herein by mechanistic or functional considerations.

The term "RNA inducing the development of stem cell characteristics" refers to RNA which when introduced into a somatic cell induces the cell to de-differentiate.

As used herein, "germ cell" refers to a reproductive cell such as a spermatocyte or an oocyte, or a cell that will develop into a reproductive cell.

As used herein, "pluripotent" refers to cells that can give rise to any cell type except the cells of the placenta or other supporting cells of the uterus.

According to the invention, standard methods can be used for production of nucleic acids, cultivation of cells and introduction of RNA into cells.

According to the invention, the term "nucleic acid" comprises deoxyribonucleic acid (DNA), ribonucleic acid (RNA), combinations thereof, and modified forms thereof. The term comprises genomic DNA, cDNA, mRNA, recombinantly produced and chemically synthesized molecules. According to the invention, a nucleic acid may be present as a single-stranded or double-stranded and linear or covalently circularly closed molecule.

A nucleic acid can, according to the invention, be isolated. The term "isolated nucleic acid" means, according to the invention, that the nucleic acid (i) was amplified in vitro, for example by a polymerase chain reaction (PCR), (ii) was produced recombinantly by cloning, (iii) was purified, for example by cleavage and separation by gel electrophoresis or (iv) was synthesized, for example by chemical synthesis.

In a preferred embodiment, a cloned nucleic acid is, according to the invention, present in a vector, with the vector optionally comprising a promoter that controls the expression of the nucleic acid. The term "vector" is used in its most general meaning and comprises any intermediate vehicles for a nucleic acid that make it possible, for example, to insert the nucleic acid into prokaryotic and/or eukaryotic cells and optionally integrate it into a genome.

Such vectors are preferably replicated and/or expressed in the cell. An intermediate vehicle can be adapted e.g. for use in electroporation, in microprojectile bombardment, in liposomal administration, in transfer by means of agrobacteria or in insertion via DNA or RNA viruses. Vectors comprise plasmids, phagemids or viral genomes.

The term "gene" relates according to the invention to a particular nucleic acid sequence, which is responsible for the production of one or more cellular products and/or for the attainment of one or more intercellular or intracellular functions. In particular the term relates to a DNA segment that codes for a specific protein or a functional or structural RNA molecule.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region, a protein or peptide coding region and a 3' non translated region. mRNA has a limited halftime in cells and in vitro. Preferably, mRNA is produced by in vitro transcription using a DNA template.

The term "expression" is used according to the invention in its most general meaning and comprises the production of RNA or of RNA and proteins/peptides, e.g. by transcription and/or translation. It also comprises partial expression of nucleic acids. Moreover, expression can be transient or stable. With reference to RNA, the term "expression" relates in particular to the production of proteins/peptides.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of the gene or the translation of the derived RNA. In certain embodiments of the invention, the expression control sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

The term "transcription" according to the invention relates to the process by which the genetic code in a DNA sequence is transcribed into RNA. The RNA may subsequently be translated into protein. According to the invention, the term "transcription" comprises "in vitro-transcription" (IVT) which relates to a process, wherein RNA, in particular mRNA, is synthesized in a cell free system in vitro preferably using appropriately prepared cell extracts. Preferably cloning vectors are used for producing transcripts which generally are designated transcription vectors.

The term "translation" according to the invention relates to the process in the ribosomes of a cell by which a strand of messenger RNA directs the assembly of a sequence of amino acids to make a protein or peptide.

In particular embodiments, the RNA that is to be introduced into a cell according to the invention comprises a population of different RNA molecules, e.g. whole-cell RNA, an RNA library, or a portion of thereof, e.g. a library of RNA molecules expressed in a particular cell type, such as undifferentiated cells, in particular stem cells such as embryonic stem cells, or a fraction of the library of RNA molecules such as RNA with enriched expression in undifferentiated cells, in particular stem cells such as embryonic stem cells relative to differentiated cells.

Thus, according to the invention, the term "RNA" may include whole-cell RNA or a fraction thereof, which may be obtained by a process comprising the isolation of RNA from cells and/or by recombinant means, in particular by in vitro transcription.

In one embodiment of the methods according to the invention, the RNA that is to be introduced into a cell is obtained by in vitro transcription of an appropriate DNA template. The promoter for controlling transcription can be any promoter for an RNA polymerase. Particular examples of RNA polymerases are the T7, T3 and SP6 RNA polymerases. Preferably the in vitro transcription according to the invention is controlled by a T7 or SP6 promoter.

A DNA template for in vitro transcription may be obtained by cloning of a nucleic acid, in particular cDNA, and introducing it into an appropriate vector for in vitro transcription. The cDNA may be obtained by reverse transcription of RNA. The cDNA containing vector template may comprise vectors carrying different cDNA inserts which following transcription results in a population of different RNA molecules optionally capable of expressing different factors or may comprise vectors carrying only one species of cDNA insert which following transcription only results in a population of one RNA species capable of expressing only one factor. Thus, it is possible to produce RNA capable of expressing a single factor only or to produce compositions of different RNAs such as RNA libraries and whole-cell RNA capable of expressing more than one factor, e.g. a composition of factors specific for embryonic stem cells. The present invention envisions the introduction of all such RNA into somatic cells.

In particular, for obtaining whole-cell RNA or a fraction thereof by in vitro transcription one can proceed as follows: 1. RNA is isolated from cells and the RNA is optionally fractionated to select a specific subspecies of RNA for further processing. 2. The RNA thus obtained is transformed into cDNA, in particular by reverse transcription. 3. The cDNA following an optional separation step to select a specific subspecies of cDNA for further processing is inserted into a vector suitable for in vitro transcription. 4. The vector containing the cDNA (optionally following linearization of the vector) is subjected to in vitro transcription. The optional step of fractionating RNA may serve to separate RNA containing a poly-A sequence from RNA not containing such sequence. Furthermore, it may serve to separate RNA according to for example size, particular patterns of expression etc. For example, if undifferentiated cells, in particular stem cells such as embryonic stem cells are used for isolating the RNA it is possible to select RNA for further processing which is specifically expressed in said cells but not, for example, in differentiated cells. A similar fractionation of cDNA is possible in step 3.

The RNA used according to the present invention may have a known composition (in this embodiment it is preferably known which factors are being expressed by the RNA) or the composition of the RNA may be partially or entirely unknown. Alternatively, the RNA used according to the present invention may have a known function or the function of the RNA may be partially or entirely unknown.

The present invention also relates to a method for screening factors which, on introduction into a somatic cell, either alone or in combination with other factors, are capable of inducing, enhancing or inhibiting reprogramming of an animal differentiated somatic cell to a cell having stem cell characteristics such as pluripotency. This method can also comprise determination of the nucleotide sequence of the RNA that causes the observed effect on the animal differentiated somatic cell.

According to the invention, the term "RNA capable of expressing" with respect to a particular factor means that the RNA, if present in the appropriate environment, preferably within a cell, can be expressed to produce said factor. Preferably, RNA according to the invention is able to interact with the cellular translation machinery to provide the factor it is capable of expressing.

RNA capable of expressing a particular factor according to the present invention includes naturally occurring RNA capable of expressing said factor and any non-naturally occurring RNA capable of expressing said factor, e.g. modified forms or variants of naturally occurring RNA capable of expressing said factor. For example, due to the degeneracy of the genetic code, the sequence of RNA can be modified without altering the sequence of the expressed factor. Furthermore, RNA may be modified to alter its stability and expression level.

The term "RNA capable of expressing" with respect to a particular factor includes compositions only containing RNA encoding the factor and compositions comprising RNA encoding the factor but also other RNA, in particular RNA encoding different proteins/peptides. Thus, the term "RNA capable of expressing" with respect to a particular factor may also include whole-cell RNA or a fraction thereof.

If according to the invention reference is made to RNA expressing more than one factor, the RNA may comprise different RNA molecules expressing different of these more than one factors. However, the present invention also includes situations wherein one RNA molecule expresses different factors, optionally linked through each other.

According to the invention, the stability and translation efficiency of the RNA introduced into a cell may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference.

For example, RNA having an unmasked poly-A sequence is translated more efficiently than RNA having a masked poly-A sequence. The term "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

In order to increase expression of the RNA used according to the present invention, it may be modified within the coding region, i.e. the sequence encoding the expressed factor, preferably without altering the sequence of the expressed factor, so as to increase the GC-content and thus, enhance translation in cells.

In further embodiments of the invention, the RNA that is to be introduced into a cell has, at its 5' end, a Cap structure or a regulatory sequence, which promotes the translation in the host cell. Preferably, RNA is capped at its 5' end by an optionally modified 7-methylguanosine attached by a 5'-5' bridge to the first transcribed nucleotide of the mRNA chain. Preferably, the 5' end of the RNA includes a Cap structure having the following general formula:

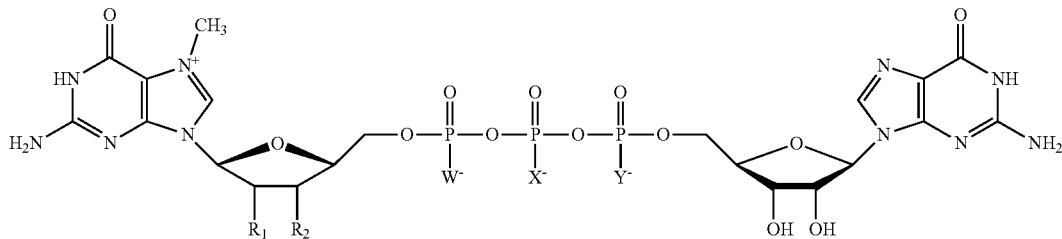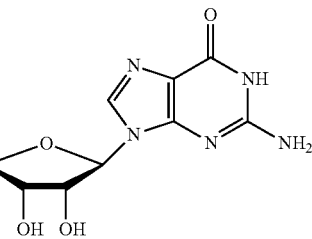

wherein $R_1$ and $R_2$ are independently hydroxy or methoxy and $W^-$, $X^-$ and $Y^-$ are independently oxygen or sulfur. In a preferred embodiment, $R_1$ and $R_2$ are hydroxy and $W^-$, $X^-$ and $Y^-$ are oxygen. In a further preferred embodiment, one of $R_1$ and $R_2$, preferably $R_1$ is hydroxy and the other is methoxy and $W^-$, $X^-$ and $Y^-$ are oxygen. In a further preferred embodiment, $R_1$ and $R_2$ are hydroxy and one of $W^-$, $X^-$ and $Y^-$, preferably $X^-$ is sulfur while the other are oxygen. In a further preferred embodiment, one of $R_1$ and $R_2$, preferably $R_2$ is hydroxy and the other is methoxy and one of $W^-$, $X^-$ and $Y^-$, preferably $X^-$ is sulfur while the other are oxygen.

In the above formula, the nucleotide on the right hand side is connected to the RNA chain through its 3' group. Preferred embodiments of the 5' Cap structure are also shown in FIG. 4A.

Those Cap structures wherein at least one of $W^-$, $X^-$ and $Y^-$ is sulfur, i.e. which have a phosphorothioate moiety, exist in different diastereoisomeric forms all of which are encompassed herein. Furthermore, the present invention encompasses all tautomers and stereoisomers of the above formula.

For example, the Cap structure having the above structure wherein $R_1$ is methoxy, $R_2$ is hydroxy, $X^-$ is sulfur and $W^-$ and $Y^-$ are oxygen exists in two diastereoisomeric forms (Rp and Sp). These can be resolved by reverse phase HPLC and are named D1 and D2 according to their elution order from the reverse phase HPLC column. According to the invention, the D1 isomer of $m_2^{7,2'-O}Gpp_sPG$ is particularly preferred.

Of course, if according to the present invention it is desired to decrease stability and/or translation efficiency of RNA, it is possible to modify RNA so as to interfere with the function of elements as described above increasing the stability and or translation efficiency of RNA.

According to the present invention, any technique useful for transferring RNA into cells may be used for introducing RNA into cells. Preferably, RNA is transfected into cells by standard techniques. Such techniques include electroporation, lipofection and microinjection. In one particularly preferred embodiment of the present invention, RNA is introduced into cells by electroporation.

Electroporation or electropermeabilization relates to a significant increase in the electrical conductivity and permeability of the cell plasma membrane caused by an externally applied electrical field. It is usually used in molecular biology as a way of introducing some substance into a cell.

Electroporation is usually done with electroporators, appliances which create an electro-magnetic field in the cell solution. The cell suspension is pipetted into a glass or plastic cuvette which has two aluminum electrodes on its sides.

For electroporation, typically a cell suspension of around 50 microliters is used. Prior to electroporation it is mixed with the nucleic acid to be transformed. The mixture is pipetted into the cuvette, the voltage and capacitance is set and the cuvette inserted into the electroporator. Preferably, liquid medium is added immediately after electroporation (in the cuvette or in an eppendorf tube), and the tube is incubated at the cells' optimal temperature for an hour or more to allow recovery of the cells and optionally expression of antibiotic resistance.

Preferably according to the invention a voltage of 200 to 300 V, preferably 230 to 270 V, more preferably around 250 V and a capacitance of 200 to 600 µF, preferably 250 to 500 µF, more preferably preferably 300 to 500 µF is used for electroporation.

According to the invention it is preferred that introduction of RNA capable of expressing certain factors as disclosed herein into somatic cells results in expression of said factors for a time period to complete the reprogramming process and in the development of cells having stem cell characteristics. Preferably, introduction of RNA capable of expression certain factors as disclosed herein into somatic cells results in expression of said factors for an extended period of time, preferably for at least 10 days, preferably for at least 11 days and more preferably for at least 12 days. To achieve such long term expression, RNA is preferably periodically introduced into the cells more than one time, preferably using electroporation. Preferably, RNA is introduced into the cells at least twice, more preferably at least 3 times, more preferably at least 4 times, even more preferably at least 5 times up to preferably 6 times, more preferably up to 7 times or even up to 8, 9 or 10 times to ensure expression of one or more factors for an extended period of time. Preferably, the time periods elapsing between the repeated introductions of the RNA are from 24 hours to 120 hours, preferably 48 hours to 96 hours. In one embodiment, time periods elapsing between the repeated introductions of the RNA are not longer than 72 hours, preferably not longer than 48 hours or 36 hours. In one embodiment, prior to the next electroporation, cells are allowed to recover from the previous electroporation. In this embodiment, the time periods elapsing between the repeated introductions of the RNA are at least 72 hours, preferably at least 96 hours, more preferably at least 120 hours. In any case, the conditions should be selected so that the factors are expressed in the cells in amount and for periods of time which support the reprogramming process.

Preferably at least 1 µg, preferably at least 1.25 µg, more preferably at least 1.5 µg and preferably up to 20 µg, more preferably up to 15 µg, more preferably up to 10 µg, more preferably up to 5 µg, preferably 1 to 10 µg, even more preferably 1 to 5 µg, or 1 to 2.5 µg of RNA for each factor is used per electroporation.

Preferably, to allow the development of cells having stem cell characteristics, cells are cultivated in the presence of one or more DNA methyltransferase inhibitors and/or one or more histone deacetylase inhibitors. Preferred compounds are selected from the group consisting of 5'-azacytidine (5'-azaC), suberoylanilide hydroxamic acid (SAHA), dexamethasone, trichostatin A (TSA) and valproic acid (VPA). Preferably, cells are cultivated in the presence of valproic acid (VPA), preferably in a concentration of between 0.5 and 10 mM, more preferably between 1 and 5 mM, most preferably in a concentration of about 2 mM.

In a preferred embodiment of the present invention, RNA is introduced into the somatic cells by repeated electroporations. Preferably, if a loss of viability of the cells occurs, previously not electroporated cells are added as carrier cells. Preferably, previously not electroporated cells are added prior to, during or after one or more of the 4$^{th}$ and subsequent, preferably, the 5$^{th}$ and subsequent electroporations such as prior to, during or after the 4$^{th}$ and 6$^{th}$ electroporation. Preferably, previously not electroporated cells are added prior to, during or after the 4$^{th}$ or 5$^{th}$ and each subsequent electroporation.

Preferably, introduction of RNA capable of expressing one or more factors into a cell causes expression of the one or more factors in the cell.

The term "transfection of RNA" relates according to the invention to the introduction of one or more nucleic acids into a cell. According to the present invention, the cell can be an isolated cell or it can form part of an organ, a tissue and/or an organism.

The term "factor" according to the invention when used in conjunction with the expression thereof by RNA includes proteins and peptides as well as derivatives and variants thereof. For example, the term "factor" comprises OCT4, SOX2, NANOG, LIN28, KLF4 and c-MYC.

The factors can be of any animal species; e.g., mammals and rodents. Examples of mammals include but are not limited to human and non-human primates. Primates include but are not limited to humans, chimpanzees, baboons, cynomolgus monkeys, and any other New or Old World monkeys. Rodents include but are not limited to mouse, rat, guinea pig, hamster and gerbil.

OCT4 is a transcription factor of the eukaryotic POU transcription factors and an indicator of pluripotency of embryonic stem cells. It is a maternally expressed Octomer binding protein. It has been observed to be present in oocytes, the inner cell mass of blastocytes and also in the primordial germ cell. The gene POU5F1 encodes the OCT4 protein. Synonyms to the gene name include OCT3, OCT4, OTF3 and MGC22487. The presence of OCT4 at specific concentrations is necessary for embryonic stem cells to remain undifferentiated.

Preferably, "OCT4 protein" or simply "OCT4" relates to human OCT4 and preferably comprises an amino acid sequence encoded by the nucleic acid according to SEQ ID NO: 1, preferably the amino acid sequence according to SEQ ID NO: 2. One skilled in the art would understand that the cDNA sequence of OCT4 as described above would be equivalent to OCT4 mRNA, and can be used for the generation of RNA capable of expressing OCT4.

Sox2 is a member of the Sox (SRY-related HMG box) gene family that encode transcription factors with a single HMG DNA-binding domain. SOX2 has been found to control neural progenitor cells by inhibiting their ability to differentiate. The repression of the factor results in delamination from the ventricular zone, which is followed by an exit from the cell cycle. These cells also begin to lose their progenitor character through the loss of progenitor and early neuronal differentiation markers.

Preferably, "SOX2 protein" or simply "SOX2" relates to human SOX2 and preferably comprises an amino acid sequence encoded by the nucleic acid according to SEQ ID NO: 3, preferably the amino acid sequence according to SEQ ID NO: 4. One skilled in the art would understand that the cDNA sequence of SOX2 as described above would be equivalent to SOX2 mRNA, and can be used for the generation of RNA capable of expressing SOX2.

NANOG is a NK-2 type homeodomain gene, and has been proposed to play a key role in maintaining stem cell pluripotency presumably by regulating the expression of genes critical to embryonic stem cell renewal and differentiation. NANOG behaves as a transcription activator with two unusually strong activation domains embedded in its C terminus. Reduction of NANOG expression induces differentiation of embryonic stem cells.

Preferably, "NANOG protein" or simply "NANOG" relates to human NANOG and preferably comprises an amino acid sequence encoded by the nucleic acid according to SEQ ID NO: 5, preferably the amino acid sequence according to SEQ ID NO: 6. One skilled in the art would understand that the cDNA sequence of NANOG as described above would be equivalent to NANOG mRNA, and can be used for the generation of RNA capable of expressing NANOG.

LIN28 is a conserved cytoplasmic protein with an unusual pairing of RNA-binding motifs: a cold shock domain and a pair of retroviral-type CCHC zinc fingers. In mammals, it is abundant in diverse types of undifferentiated cells. In pluripotent mammalian cells, LIN28 is observed in RNase-sensitive complexes with Poly(A)-Binding Protein, and in polysomal fractions of sucrose gradients, suggesting it is associated with translating mRNAs.

Preferably, "LIN28 protein" or simply "LIN28" relates to human LIN28 and preferably comprises an amino acid sequence encoded by the nucleic acid according to SEQ ID NO: 7, preferably the amino acid sequence according to SEQ ID NO: 8. One skilled in the art would understand that the cDNA sequence of LIN28 as described above would be equivalent to LIN28 mRNA, and can be used for the generation of RNA capable of expressing LIN28.

Krueppel-like factor (KLF4) is a zinc-finger transcription factor, which is strongly expressed in postmitotic epithelial cells of different tissues, e.g. the colon, the stomach and the skin. KLF4 is essential for the terminal differentiation of these cells and involved in the cell cycle regulation.

Preferably, "KLF4 protein" or simply "KLF4" relates to human KLF4 and preferably comprises an amino acid sequence encoded by the nucleic acid according to SEQ ID NO: 9, preferably the amino acid sequence according to SEQ ID NO: 10. One skilled in the art would understand that the cDNA sequence of KLF4 as described above would be equivalent to KLF4 mRNA, and can be used for the generation of RNA capable of expressing KLF4.

MYC (cMYC) is a protooncogene, which is overexpressed in a wide range of human cancers. When it is specifically-mutated, or overexpressed, it increases cell proliferation and functions as an oncogene. MYC gene encodes for a transcription factor that regulates expression of 15% of all genes through binding on Enhancer Box sequences (E-boxes) and recruiting histone acetyltransferases (HATs). MYC belongs to MYC family of transcription factors, which also includes N-MYC and L-MYC genes. MYC-family transcription factors contain the bHLH/LZ (basic Helix-Loop-Helix Leucine Zipper) domain Preferably, "cMYC protein" or simply "cMYC" relates to human cMYC and preferably comprises an amino acid sequence encoded by the nucleic acid according to SEQ ID NO: 11, preferably the amino acid sequence according to SEQ ID NO: 12. One skilled in the art would understand that the cDNA sequence of cMYC as described above would be equivalent to cMYC mRNA, and can be used for the generation of RNA capable of expressing cMYC.

A reference herein to specific factors such as OCT4, SOX2, NANOG, LIN28, KLF4 or c-MYC or to specific sequences thereof is to be understood so as to also include all variants of these specific factors or the specific sequences thereof as described herein. In particular, it is to be understood so as to also include all splice variants, posttranslationally modified variants, conformations, isoforms and species homologs of these specific factors/sequences which are naturally expressed by cells.

According to the present invention, the term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Proteins and peptides described according to the invention may be isolated from biological samples such as tissue or cell homogenates and may also be expressed recombinantly in a multiplicity of pro- or eukaryotic expression systems.

For the purposes of the present invention, "variants" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

"Conservative substitutions" may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Preferably the degree of similarity, preferably identity between a specific amino acid sequence described herein and an amino acid sequence which is a variant of said specific amino acid sequence will be at least 70%, preferably at least 80%, preferably at least 85%, even more preferably at least 90% or most preferably at least 95%, 96%, 97%, 98% or 99%. The degree of similarity or identity is given preferably for a region of at least about 20, at least about 40, at least about 60, at least about 80, at least about 100, at least about 120, at least about 140, at least about 160, at least about 200 or 250 amino acids. In preferred embodiments, the degree of similarity or identity is given for the entire length of the reference amino acid sequence.

The amino acid variants described above may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, "variants" of proteins and peptides also comprise single or multiple substitutions, deletions and/or additions of any molecules associated with the protein or peptide, such as carbohydrates, lipids and/or proteins or peptides. The term "variants" also extends to all functional chemical equivalents of said proteins and peptides.

According to the invention, a variant of a protein or peptide preferably has a functional property of the protein or peptide from which it has been derived. Such functional properties are described above for OCT4, SOX2, NANOG, LIN28, KLF4 and c-MYC, respectively. Preferably, a variant of a protein or peptide has the same property in reprogramming an animal differentiated cell as the protein or peptide from which it has been derived. Preferably, the variant induces or enhances reprogramming of an animal differentiated cell.

The methods of the present invention can be used to effect de-differentiation of any type of somatic cell. Cells that may be used include cells that can be de-differentiated or reprogrammed by the methods of the present invention, in particular cells that are fully or partially differentiated, more preferably terminally differentiated. Preferably, the somatic cell is a diploid cell derived from pre-embryonic, embryonic, fetal, and post-natal multi-cellular organisms. Examples of cells that may be used include but are not limited to fibroblasts, such as fetal and neonatal fibroblasts or adult fibroblasts, keratinocytes, in particular primary keratinocytes, more preferably keratinocytes derived from hair, B cells, T cells, dendritic cells, adipose cells, epithelial cells, epidermal cells, chondrocytes, cumulus cells, neural cells, glial cells, astrocytes, cardiac cells, esophageal cells, muscle cells, melanocytes, hematopoietic cells, osteocytes, macrophages, monocytes, and mononuclear cells.

The cells with which the methods of the invention can be used can be of any animal species; e.g., mammals and rodents. Examples of mammalian cells that can be de-differentiated and re-differentiated by the present invention include but are not limited to human and non-human primate cells. Primate cells with which the invention may be performed include but are not limited to cells of humans, chimpanzees, baboons, cynomolgus monkeys, and any other New or Old World monkeys. Rodent cells with which the invention may be performed include but are not limited to mouse, rat, guinea pig, hamster and gerbil cells.

The term "organism" according to the invention relates to any biological unit that is capable of multiplying or transmitting genetic material and comprises plants and animals, and microorganisms such as bacteria, yeasts, fungi and viruses. The term "organism" includes but is not limited to a human being, a nonhuman primate or another animal, in particular a mammal such as a cow, horse, pig, sheep, goat, dog, cat or a rodent such as a mouse and rat. In a particularly preferred embodiment, the organism is a human being.

De-differentiated cells prepared according to the present invention are expected to display many of the same requirements as pluripotent stem cells and can be expanded and maintained under conditions used for embryonic stem cells, e.g. ES cell medium or any medium that supports growth of the embryonic cells. Embryonic stem cells retain their pluripotency in vitro when maintained on inactivated fetal fibroblasts such as irradiated mouse embryonic fibroblasts or human fibroblasts (e.g., human foreskin fibroblasts, human skin fibroblasts, human endometrial fibroblasts, human oviductal fibroblasts) in culture. In one embodiment, the human feeder cells may be autologous feeder cells derived from the same culture of reprogrammed cells by direct differentiation.

Furthermore, human embryonic stem cells can successfully be propagated on Matrigel in a medium conditioned by mouse fetal fibroblasts. Human stem cells can be grown in culture for extended period of time and remain undifferentiated under specific culture conditions.

In certain embodiments, the cell culture conditions may include contacting the cells with factors that can inhibit differentiation or otherwise potentiate de-differentiation of cells, e.g., prevent the differentiation of cells into non-ES cells, trophectoderm or other cell types.

De-differentiated cells prepared according to the present invention can be evaluated by methods including monitoring changes in the cells' phenotype and characterizing their gene and protein expression. Gene expression can be determined by RT-PCR, and translation products can be determined by immunocytochemistry and Western blotting. In particular, de-differentiated cells can be characterized to determine the pattern of gene expression and whether the reprogrammed cells display a pattern of gene expression similar to the expression pattern expected of undifferentiated, pluripotent control cells such as embryonic stem cells using techniques well known in the art including transcriptomics.

The expression of the following genes of de-differentiated cells can be assessed in this respect: OCT4, NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (TERT), embryonic antigen-3 (SSEA-3), SSEA-4, tumor-related antigen-1-60 (TRA-1-60), TRA-1-81, and TRA-2-49/6E The undifferentiated or embryonic stem cells to which the reprogrammed cells may be compared may be from the same species as the differentiated somatic cells. Alternatively, the undifferentiated or embryonic stem cells to which the reprogrammed cells may be compared may be from a different species as the differentiated somatic cells.

In some embodiments, a similarity in gene expression pattern exists between a reprogrammed cell and an undifferentiated cell, e.g., embryonic stem cell, if certain genes specifically expressed in an undifferentiated cell are also expressed in the reprogrammed cell. For example, certain genes, e.g., telomerase, that are typically undetectable in differentiated somatic cells may be used to monitor the extent of reprogramming. Likewise, for certain genes, the absence of expression may be used to assess the extent of reprogramming.

Self-renewing capacity, marked by induction of telomerase activity, is another characteristic of stem cells that can be monitored in de-differentiated cells.

Karyotypic analysis may be performed by means of chromosome spreads from mitotic cells, spectral karyotyping, assays of telomere length, total genomic hybridization, or other techniques well known in the art.

Using the present invention, RNA encoding appropriate factors is incorporated into one or more somatic cells, e.g. by electroporation. After incorporation, cells are preferably cultured using conditions that support maintenance of de-differentiated cells (i.e. stem cell culture conditions). The de-differentiated cells can then be expanded and induced to re-differentiate into different type of somatic cells that are needed for cell therapy. De-differentiated cells obtained according to the present invention can be induced to differentiate into one or more desired somatic cell types in vitro or in vivo.

Preferably, the de-differentiated cells obtained according to the present invention may give rise to cells from any of three embryonic germ layers, i.e., endoderm, mesoderm, and ectoderm. For example, the de-differentiated cells may differentiate into skeletal muscle, skeleton, dermis of skin, connective tissue, urogenital system, heart, blood (lymph cells), and spleen (mesoderm); stomach, colon, liver, pancreas, urinary bladder; lining of urethra, epithelial parts of trachea, lungs, pharynx, thyroid, parathyroid, intestine (endoderm); or central nervous system, retina and lens, cranial and sensory, ganglia and nerves, pigment cells, head connective tissue, epidermis, hair, mammary glands (ectoderm). The de-differentiated cells obtained according to the present invention can be re-differentiated in vitro or in vivo using techniques known in the art.

In one embodiment of the present invention, the reprogrammed cells resulting from the methods of this invention are used to produce differentiated progeny. Thus, in one aspect, the present invention provides a method for producing differentiated cells, comprising: (i) obtaining reprogrammed cells using the methods of this invention; and (ii) inducing differentiation of the reprogrammed cells to produce differentiated cells. Step (ii) can be performed in vivo or in vitro. Furthermore, differentiation can be induced through the presence of appropriate differentiation factors which can either be added or are present in situ, e.g. in a body, organ or tissue into which the reprogrammed cells have been introduced. The differentiated cells can be used to derive cells, tissues and/or organs which are advantageously used in the area of cell, tissue, and/or organ transplantation. If desired, genetic modifications can be introduced, for example, into somatic cells prior to reprogramming. The differentiated cells of the present invention preferably do not possess the pluripotency of an embryonic stem cell, or an embryonic germ cell, and are, in essence, tissue-specific partially or fully differentiated cells.

One advantage of the methods of the present invention is that the reprogrammed cells obtained by the present invention can be differentiated without prior selection or purification or establishment of a cell line. Accordingly in certain embodiments, a heterogeneous population of cells comprising reprogrammed cells are differentiated into a desired cell type. In one embodiment, a mixture of cells obtained from the methods of the present invention is exposed to one or more differentiation factors and cultured in vitro.

Methods of differentiating reprogrammed cells obtained by the methods disclosed herein may comprise a step of permeabilization of the reprogrammed cell. For example, cells generated by the reprogramming techniques described herein, or alternatively a heterogeneous mixture of cells comprising reprogrammed cells, may be permeabilized before exposure to one or more differentiation factors or cell extract or other preparation comprising differentiation factors.

For example, differentiated cells may be obtained by culturing undifferentiated reprogrammed cells in the presence of at least one differentiation factor and selecting differentiated cells from the culture. Selection of differentiated cells may be based on phenotype, such as the expression of certain cell markers present on differentiated cells, or by functional assays (e.g., the ability to perform one or more functions of a particular differentiated cell type).

In another embodiment, the cells reprogrammed according to the present invention are genetically modified through the addition, deletion, or modification of their DNA sequence(s).

The reprogrammed or de-differentiated cells prepared according to the present invention or cells derived from the reprogrammed or de-differentiated cells are useful in research and in therapy. Reprogrammed pluripotent cells may be differentiated into any of the cells in the body including, without limitation, skin, cartilage, bone skeletal muscle, cardiac muscle, renal, hepatic, blood and blood forming, vascular precursor and vascular endothelial, pancreatic beta, neurons, glia, retinal, neuronal, intestinal, lung, and liver cells.

The reprogrammed cells are useful for regenerative/reparative therapy and may be transplanted into a patient in need thereof. In one embodiment, the cells are autologous with the patient.

The reprogrammed cells provided in accordance with the present invention may be used, for example, in therapeutic strategies in the treatment of cardiac, neurological, endocrinological, vascular, retinal, dermatological, muscular-skeletal disorders, and other diseases.

For example, and not intended as a limitation, the reprogrammed cells of the present invention can be used to replenish cells in animals whose natural cells have been depleted due to age or ablation therapy such as cancer radiotherapy and chemotherapy. In another non-limiting example, the reprogrammed cells of the present invention are useful in organ regeneration and tissue repair. In one embodiment of the present invention, reprogrammed cells can be used to reinvigorate damaged muscle tissue including dystrophic muscles and muscles damaged by ischemic events such as myocardial infarcts. In another embodiment of the present invention, the reprogrammed cells disclosed herein can be used to ameliorate scarring in animals, including humans, following a traumatic injury or surgery. In this embodiment, the reprogrammed cells of the present invention are administered systemically, such as intravenously, and migrate to the site of the freshly traumatized tissue recruited by circulating cytokines secreted by the damaged cells. In another embodiment of the present invention, the reprogrammed cells can be administered locally to a treatment site in need of repair or regeneration.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illustrate the invention and does not pose a limitation on the scope of the invention otherwise claimed. No language in the specification should be construed as indicating any non-claimed element essential to the practice of the invention.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Example 1: Production of IVT RNA

The first step in the production of IVT RNA comprises linearization of a plasmid containing the coding sequence for a particular factor and having an SP6 promoter or T7 promoter before the start codon, starting from which an in vitro transcription is possible. To this end, restriction enzymes are used, for example. Following linearization, the enzyme is inactivated by phenol-chloroform precipitation and removed. For this, an isovolume of a mixture of phenol and chloroform is added and mixed thoroughly.

Brief centrifugation at 10 000×g provides separation into a lower organic phase and an upper aqueous phase, which contains the DNA. The latter is transferred to a new reaction vessel. Then the aqueous phase is mixed with an isovolume of pure chloroform, to remove any phenol residues. After centrifugation, the aqueous phase is removed and precipitated for 2 h by adding two isovolumes of ethanol and 10% v/v 3M sodium acetate pH 4.5 at −20° C. The DNA is sedimented by centrifugation for 45 min at 10 000×g at 4° C., washed with 70% ethanol for removal of salts, and is taken up in a suitable volume of RNAse-free water. Gel electrophoresis is used to verify that linearization was successful and complete. The concentration of the DNA is determined photometrically at 260 nm. For determination of the purity of the DNA, in addition the optical density is measured at 280 nm to obtain the OD260/280 ratios.

10 µg of linearized DNA is used for the in vitro transcription. For this, 40 µl dNTPs, with 4/5 of the dGTP additionally provided with a Cap-structure, 10 µl 10× buffer, 20 µl dTT and 10 µl of T7 or SP6 polymerase are incubated for 2 h at 37° C. The polymerases bind to their T7 or SP6 recognition sequences, which are located 5' from the ORF that is to be transcribed, and synthesize the complementary RNA strand.

The IVT RNA is purified with the MegaClear Kit. For this, it is taken up in a binding buffer concentrate, containing the necessary salts for optimal binding of the RNA to the silica membrane. Addition of ethanol removes water from the RNA hydration shell. The mixture is loaded in a silica column and centrifuged at 10 000×g for 2 min. The RNA binds to the column, whereas impurities, e.g. enzyme residues, are washed away. After several washing steps, the purified RNA is eluted. The elution buffer is preheated to 95° C. to make elution more efficient.

Quality control and quantification are performed by gel electrophoresis and by photometry.

Example 2: Electroporation of Cells

The principle of electroporation is based on disturbing the transmembrane potential of the cells by a brief current pulse. The alteration of the transmembrane potential by an external stimulus is described by the following equation:

$$\Delta V_m = fE_{ext} r \cos \phi$$

$V_m$ is the transmembrane potential and f is a form factor, which describes the influence of the cell on the extracellular field distribution. $fE_{ext}$ describes the applied electric field, r the cell radius and $\phi$ the angle to the externally applied electric field. Factor f is often given as 1.5, though it depends on many other factors. The electroporation of the cells is successful if the applied electric field exceeds the capacity of the cell membrane, i.e. $\Delta V_m$ is greater than a threshold value $\Delta V_s$, given as 1V (Kinosita, K., Jr. and Tsong, T. Y. (1977) Nature 268, 438-441). Since construction of the cell membrane as a bilayer is a feature that is common to eukaryotic cells, this value shows little variation for different cell lines.

Through dielectric breakdown of the transmembrane potential, transiently hydrophilic pores are formed, through which water penetrates into the cell, transporting molecules e.g. nucleic acids into the cells (Weaver, J. C. (1995) Methods Mol. Biol. 55, 3-28; Neumann, E. et al. (1999) Bioelectrochem. Bioenerg. 48, 3-16).

Prior to electroporation, the adherent cells used are cultivated up to semi-confluence, washed with PBS and detached from the cell culture flasks with trypsin. The cells are transferred to medium with 10% FCS (fetal calf serum) and centrifuged for 8 min at 500×g. The pellet is resuspended in the serum free medium X-Vivo and centrifuged again for 8 min at 500×g. This washing operation is carried out two more times in order to remove residues of FCS, which would interfere with subsequent electroporation.

After washing, the cells are adjusted in 250 µl to the desired cell density, transferred to the electroporation cuvettes and placed on ice. After adding the appropriate amount of in vitro transcribed RNA and stirring thoroughly, electroporation is carried out at 200V and 250 µF. Then the cells are transferred immediately to the adequate nutrient medium for incubation.

According to the invention, it was possible to transfect cell lines with an efficiency of up to 90% or even more.

Moreover, an influence of cell count on transfection efficiency could be excluded in a range between $2 \times 10^6$ and $2 \times 10^7$ cells. The electroporation conditions also do not have a decisive influence on transfection efficiency in the range tested Stability of the RNA was demonstrated over a period of 24 h, whereas the protein can be detected in the cells over a period of 48-72 h, depending on its half-life.

It could be shown that there is a direct dependency between the amount of transfected RNA and the amount of protein available.

Example 3: Stability of Proteins Expressed by Transfected RNA

Figure 1:
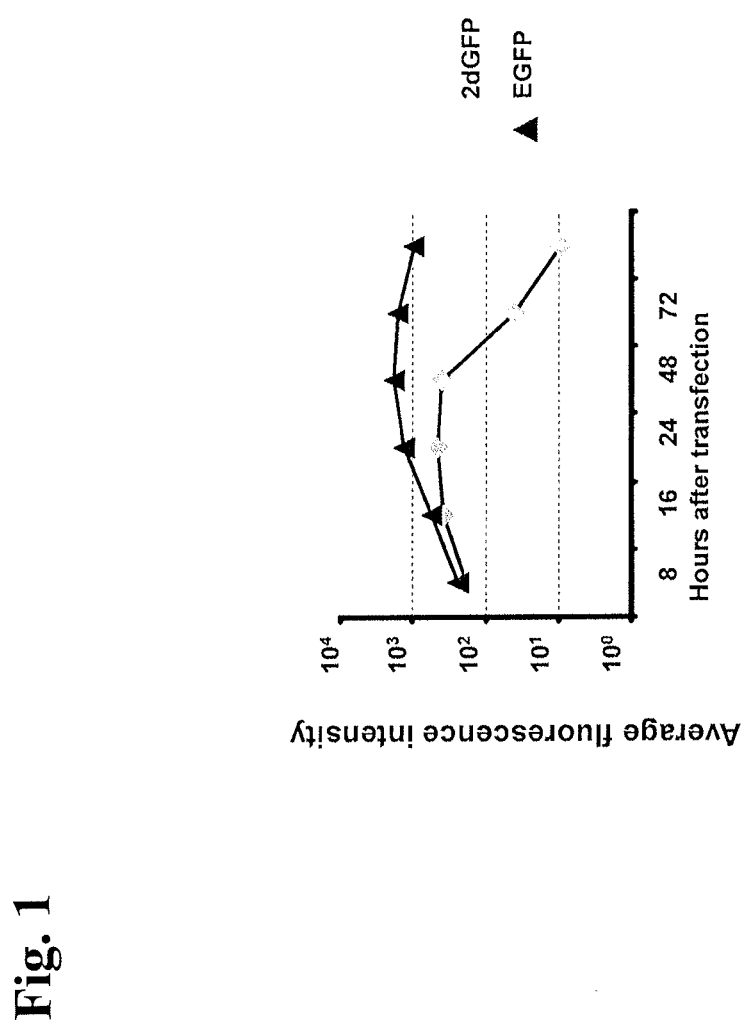
FIG. 1: Determination of the influence of time on the amount of transcript and protein following transfection of 786-0 cells with 20 μg eGFP IVT (in vitro transcribed) RNA and 2dGFP IVT RNA, respectively. Determination of the average fluorescence intensity of eGFP using FACS-Kalibur.

We next examined for how long proteins with different halftimes following transfer of IVT RNA can be stably detected in cells. 786-0 cells were transfected with 20 µg eGFP IVT RNA and 2dGFP IVT RNA, respectively, and the fluorescence intensity was measured in the time course of 3 h to 120 h. The eGFP protein has a halftime of 16 h, while the halftime of the destabilized variant 2dGFP due to the integration of a PEST amino acid sequence effecting protein degradation is reduced to 2 h (Clontech, 1998). The experiment showed that already after 4 h a substantial amount of translated protein was detectable which further increased until 24 h after transfection. The amount of eGFP protein remains relatively constant for more than 120 h. Even the destabilized 2dGFP shows stable protein expression for 48 h (FIG. 1). In order to induce protein expression of 2dGFP which is stable over a long period of time RNA can be transfected every 48 h.

Example 4: Examination of Effects Due to the Methodology Following RNA Electroporation We next examined which unspecific effects are induced by electroporation and introduction of single stranded RNA into cells. These effects could superimpose the cell differentiation induced by a specific gene product transferred as IVT RNA. $2 \times 10^7$ 786-0 cells were transfected with 20 µg eGFP IVT RNA and were cultivated for further 8 h, 24 h and 72 h. A comparison with untransfected cells did not show a change in growth behaviour and did not show an intensified apoptosis. The portion of living cells following transfection in each case was about 95%.

In a further step, RNA was extracted from the cells and used for preparing probes. The probes were hybridized on a cDNA microarray chip with several hundreds of genes. This was followed by a basic evaluation using the program ImaGene software version 4.1 (BioDiscovery, Los Angeles, CA). Impurities on the array which were visible to the naked eye were masked manually. Following normalization using the control genes which were also spotted on the array, the relative expression levels compared to the reference were obtained. The number of significantly regulated genes is shown in Table 1.

TABLE 1

Number of significantly regulated genes in $2 \times 10^7$ 786-0 cells which were transfected with 20 µg eGFP IVT RNA compared to non-transfected control cells. Only a regulation of > 2 and 0.5, respectively, was considered a significant change.

| Factor of regulation | Number of regulated genes after 8 h | Number of regulated genes after 24 h | Number of regulated genes after 72 h |
|---|---|---|---|
| >2 | 10 (0.87%) | 0 | 0 |
| <0.5 | 48 (4.16%) | 15 (1.3%) | 0 |

The number of significantly regulates genes was moderate and decreased over time. 24 h after electroporation and introduction of single stranded RNA into the cells only 15 genes (1.3%) are still differentially expressed. The eGFP-specific regulation of these genes was excluded by means of an additional analysis of cells which were transfected using irrelevant IVT RNA. Accordingly, the dysfunction of the transcriptome of the cells in terms of an unspecific regulation of genes which is inherently caused by the methodology is low. Reprogramming of cells by transfection with IVT RNA thus is expected to be not affected by difficulties which are inherent to the methodology or only to a very small extent.

Example 5: Reprogramming of Cells by Means of Introduction of RNA Coding for Transcription Factors To examine whether the introduction of genes can be used for changing the cellular program, we have analyzed the effect of the transfection of the oncogenic transcription factors SYT-SSX1 and SYT-SSX2 which result from the translocation t(X;18)(p11.2;q11.2) (Clark et al., 1994; Crew et al., 1995) and are detectable in more than 90% of the synovial sarcomas (Sreekantaiah et al., 1994). The molecular changes caused by the transfection of SYT-SSX1 and SYT-SSX2 IVT RNA were analyzed using Affymetrix oligonucleotide microarrays. The different constructs each were transfected in triplicate. Transfection with eGFP was performed in order to be able to examine the transfection efficiency in the fluorescence microscope. After 8 h a transfection efficiency of more than 95% was determined (data not shown). The cells were harvested after 8 h, 24 h and 72 h, respectively, and the RNA was extracted. For analysing the molecular changes in the cells following RNA transfer of the listed genes we used Affymetrix oligonucleotide microarrays which enabled the simultaneous examination of changes in expression of 22,000 genes.

Figure 2A:
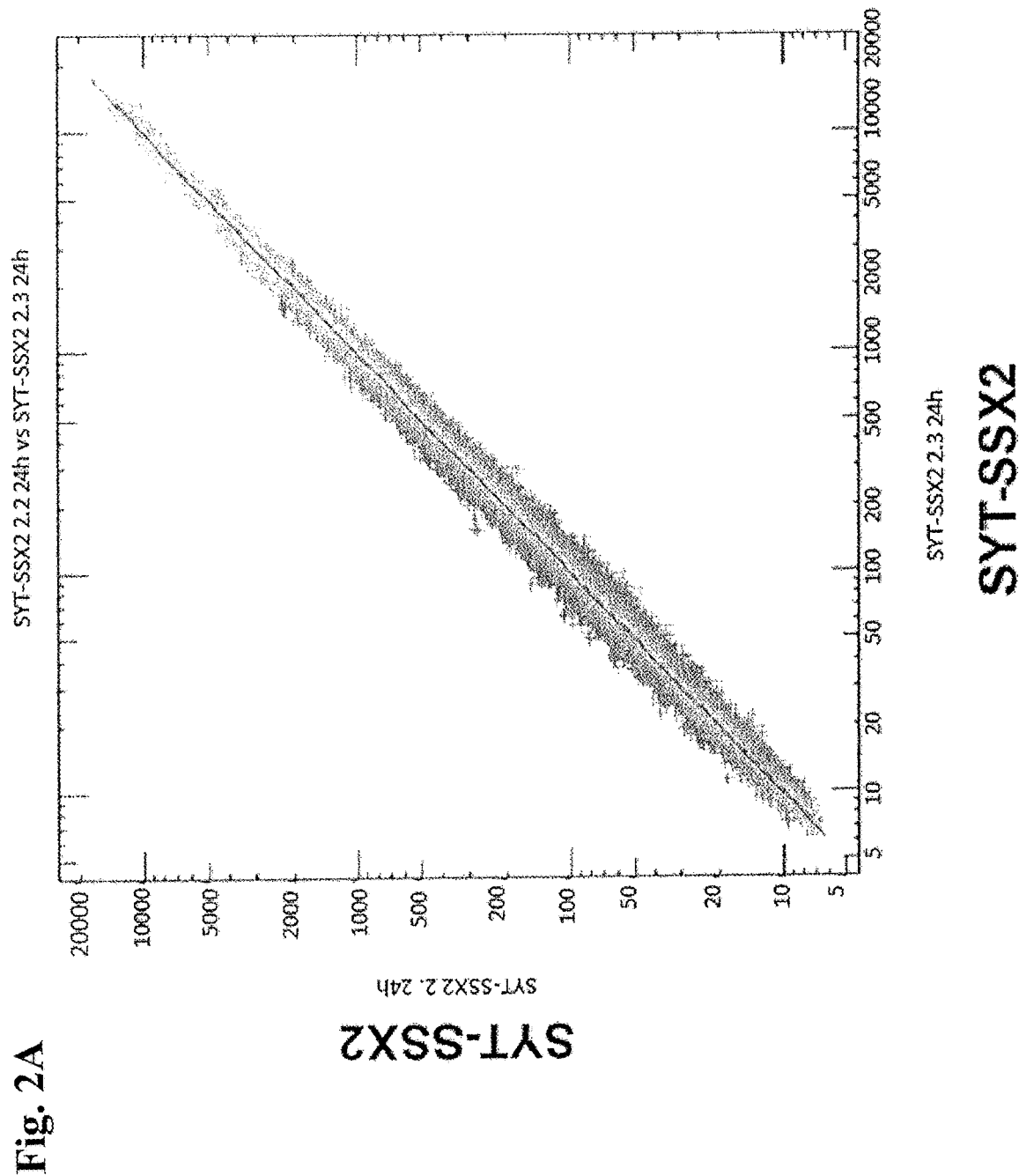
FIGS. 2A and 2B: Scatter blot of all genes for determining the similarity of the duplicates.
Figure 2B:
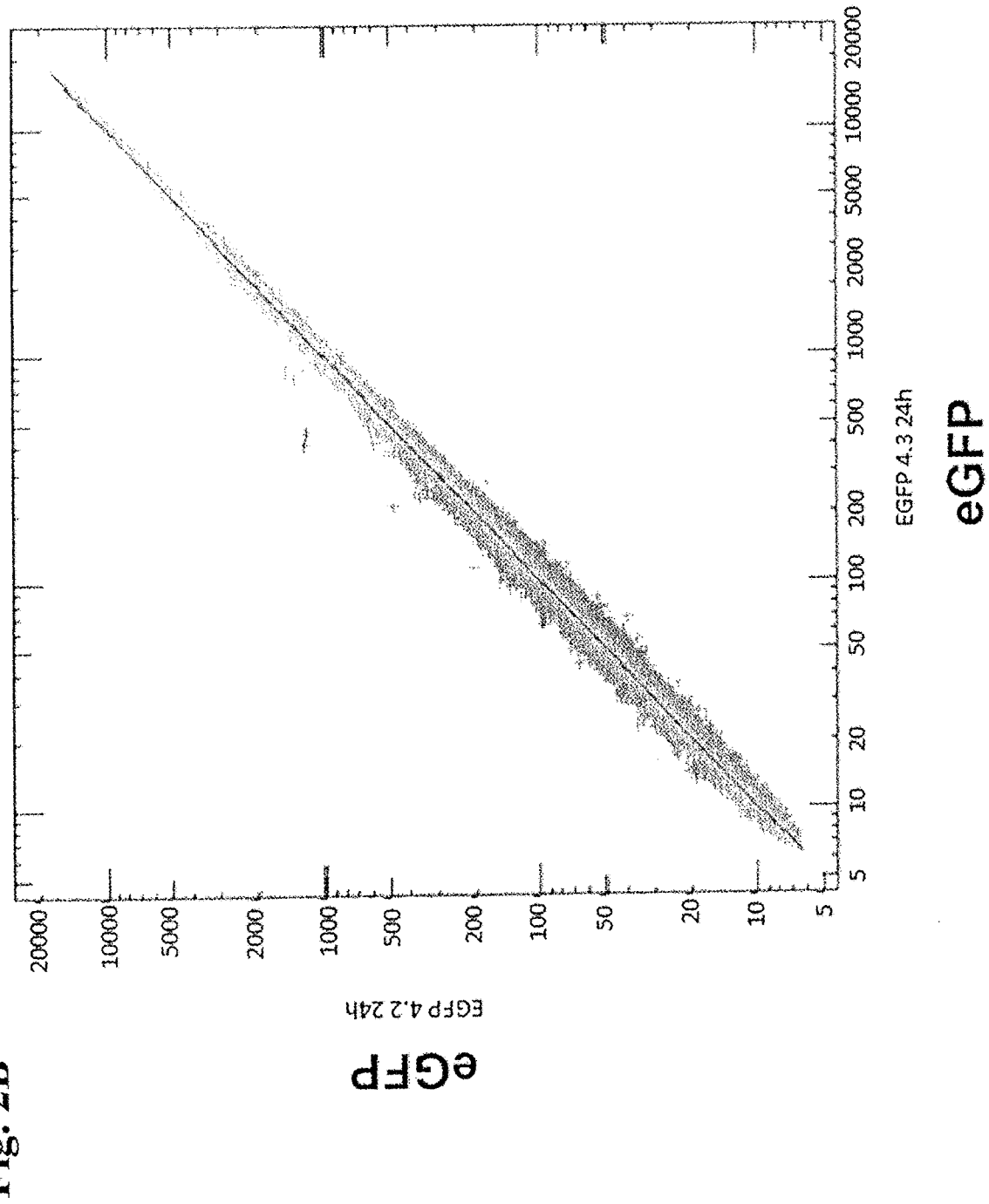

For analysing cells transfected with SYT-SSX2 and eGFP two human genome U133A arrays were hybridized at 8 h and 24 h in each case. SSX2 and SYT-SSX1 were examined in single determinations at 8 h and 24 h. Evaluation of the data was done using the Software Microarray Suite 5.0 as well as ArrayAssist (FIG. 2). The number of the significantly regulated genes in the comparison of the duplicates among each other was zero. This resulted in a sufficient confidence with respect to the reproducibility of the results such that also the microarray results of the transfectants which were only represented by single determinations (SYT-SSX1 and SSX2) could be included in the analysis.

Figure 3A:
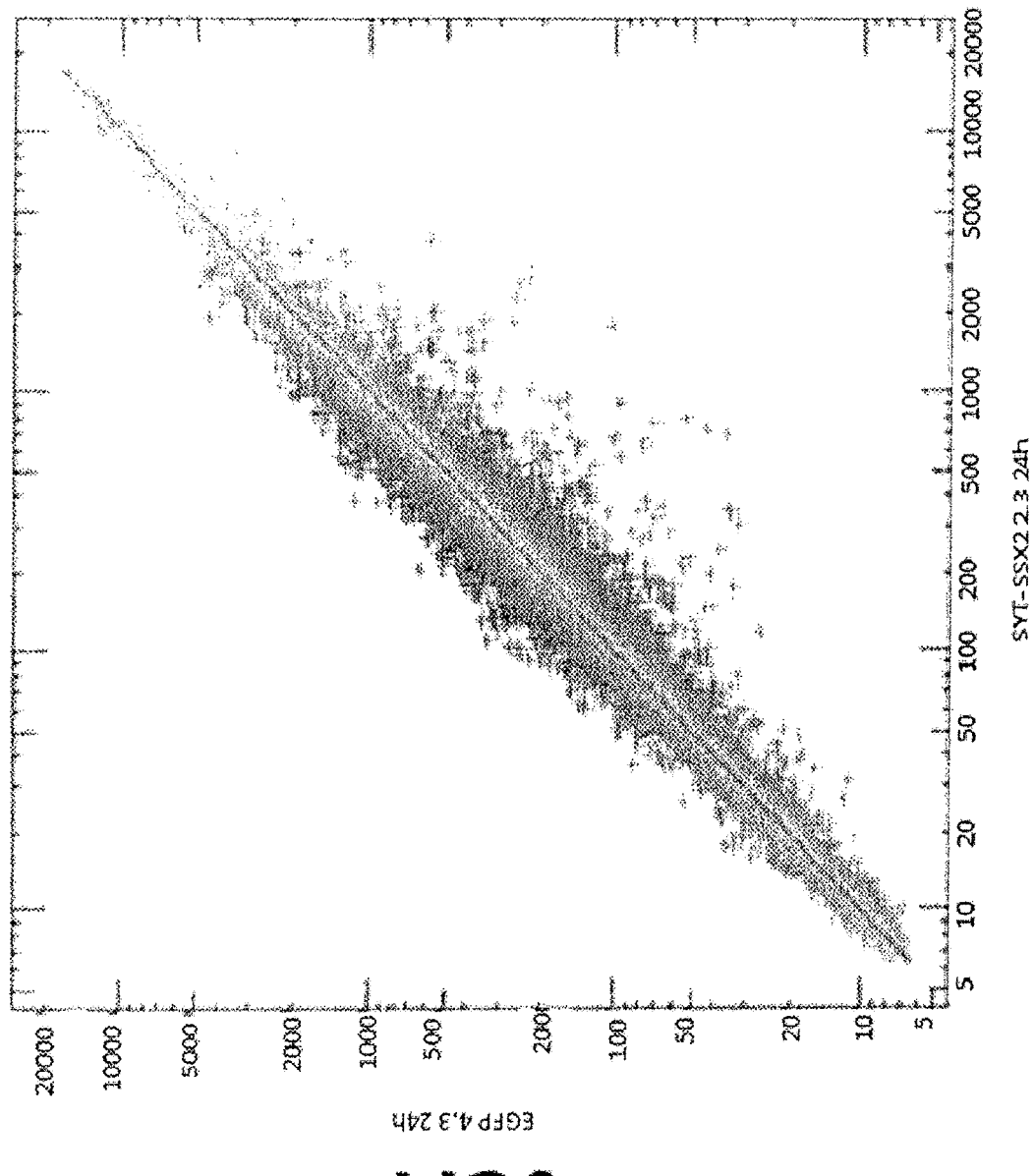
FIGS. 3A and 3B: Representation of the genes regulated by SYT-SSX2.

For determining the genes which are significantly regulated by SYT-SSX2, the expression values of the eGFP transfected cells were taken as basis and the expression pattern of the SSX2, SYT-SSX1 and SYT-SSX2 IVT RNA transfected cells were compared thereto (FIG. 3). Evaluation of the data was performed using the programs Microarray Suite 5.0 and ArrayAssist. FIG. 3a exemplarily demonstrates the differential expression of genes by SYT-SSX2.

Figure 3B:
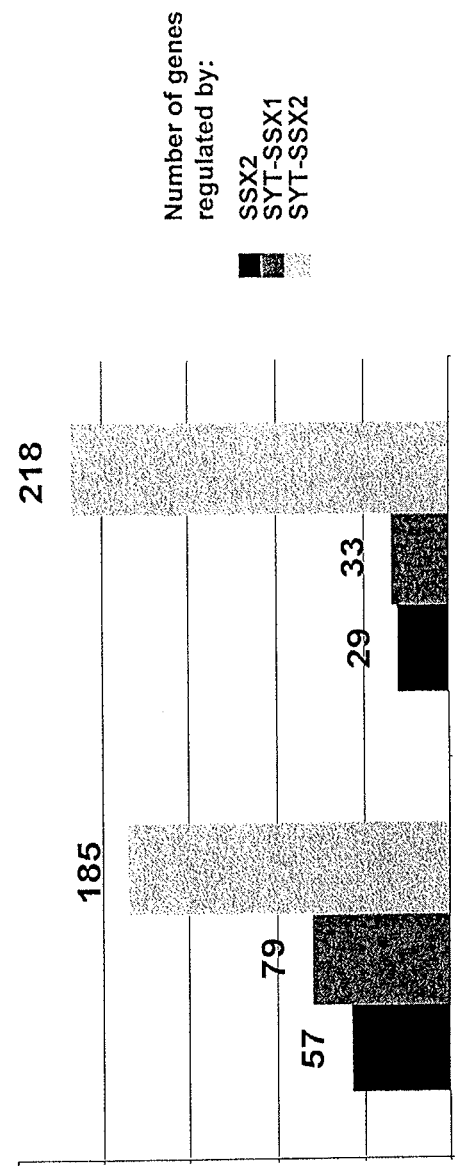

For evaluation, a regulation by at least a factor of two was taken as a basis which corresponds to the range of sensitivity of the system. A value of p=5% was considered as a criterion of significance. Under these conditions, 185 genes could be detected in the SYT-SSX2 transfected cells after 8 h and 218 genes could be detected after 24 h. The portion of genes which are regulated after 8 h as well as after 24 h is 41.3% (FIG. 3b).

The regulated genes can be assigned to different groups on the basis of their function. These are, for example, growth factors, neuronal genes, tumor associated genes, collagens, as well as those which are involved in the processes of signal transduction, cell adhesion, cell development and cell differentiation as well as in the regulation of the cell cycle.

In this respect it is noticeable that the portion of overexpressed genes is significantly higher than the portion of suppressed genes. The genes which are regulated by SYT-SSX1 are >95% identical to those which are also regulated by SYT-SSX2.

The differential expression in vivo of the analyzed genes could be clearly confirmed in synovial sarcomas. The increased expression of BMP7 and EPHA4 was already described in other studies (Nagayama et al., 2002). Overexpression in synovial sarcomas was also detectable for FGFR4, p57, BMP5 and PGF.

These studies show that the transfer of RNA of transcription factors can be successfully used to change differentiation of cells.

Example 6: Reprogramming of Cells by Means of Introduction of RNA Coding for Transcription Factor Cocktails In-vitro translated mRNA (IVT-RNA) encoding the TFs cocktail OCT4, SOX2, KLF4 and c-MYC (OSKM) or OCT4, SOX2, LIN28 and NANOG (OSLN) was electrotransferred into the cytoplasm of human or murine fibroblasts.

In a first set of experiments, we optimized the electroporation parameters using IVT-RNA encoding eGFP for human newborn foreskin fibroblasts (CCD1079Sk) and mouse embryonic fibroblasts (MEF).

As a general measure to increase the stability of the IVT-RNA constructs and the protein translation, the nucleotide sequence of the TFs has been codon optimized to increase the GC-content and to enhance translation in human or mouse cells. Since the expression efficiency and stability of IVT-RNA is mainly dependent on the 5'-CAP structure, we evaluated the effect of three different 5'-Cap-Structures (FIG. 4) that are well established in our lab on the expression of luciferase in CCD1079Sk-cells.

We found that the efficiency of electroporation is consistently higher than 90%, which is higher than the retroviral transduction efficiencies published by others (Takahasi et al., 2006; Takahasi et al., 2007). Especially, one has to consider that an infection efficiency of 80% for one retroviral vector means that cotranduction efficiencies for all 4 required vectors will be lower ($0.8^4=0.4$). Our approach, the co-electroporation of the 4 TFs will ensure the transfer of all 4 factors to more than 90% of the cells.

Figure 5:
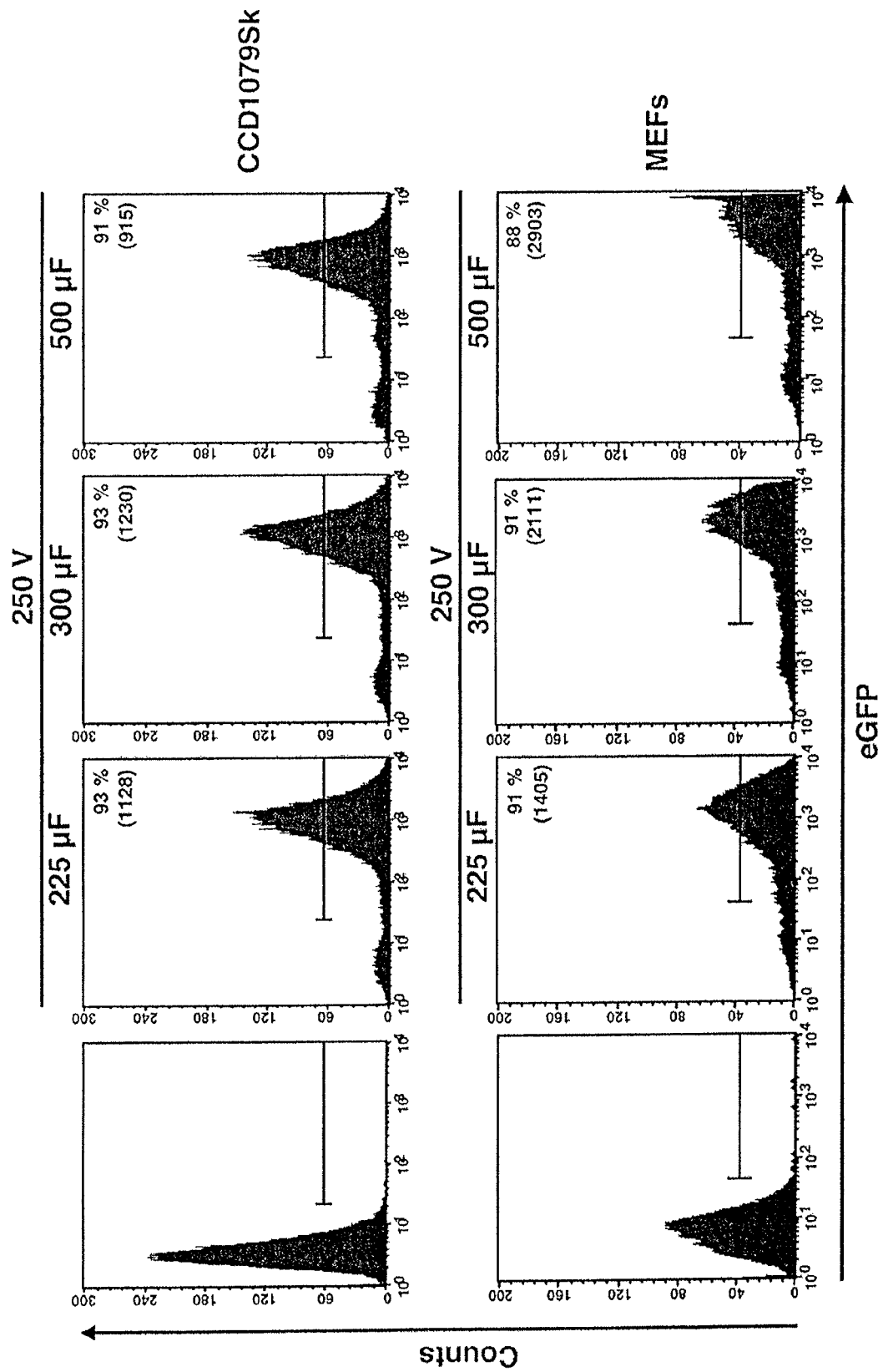
FIG. 5: Electroporation of human fibroblasts (CCD1079Sk) and mouse embryonic fibroblasts (MEFs).

We observed that the highest efficiency is achieved when CCD1079SK cells or MEFs are electroporated with 300 µF/250V or 500 µF/250V respectively regarding the mean fluorescence of eGFP (which corresponds to the highest expression level) (FIG. 5).

We furthermore found that the IVT-mRNA with D1 cap structure displayed the highest and most stable expression of luciferase in CCD1079Sk cells (FIG. 6) and was therefore chosen for the subsequent experiments. The IVT-mRNA with D2 cap structure displayed higher and more stable expression of luciferase than IVT-mRNA with ARCA cap structure.

Next we examined the intracellular amount of the electroporated RNA and expression levels of these exogenous mRNA constructs encoding the six TFs SOX2, OCT4, KLF4, cMYC, NANOG, and LIN28. Oligonucleotides specific for the codon-optimized constructs were used in qRT-PCR studies. In the same set of experiments we determined the half-life of the IVT-RNA and the encoded proteins in time course experiments.

We found that:
  (i) high levels of IVT-RNA can be detected by qRT-PCR after 24 h in electroporated CCD1079Sk cells (FIG. 7),
  (ii) the IVT-RNA of all six transcription factors is well detectable even 168 h post electroporation (FIG. 7),
  (iii) the IVT-RNA encoding the four TFs SOX2, OCT4, KLF4, and cMYC (OSKM) are translated to high protein levels 24 h post electroporation as monitored by western blot analysis (FIG. 8), (iv) OCT4—together with SOX2 the most important TF for reprogramming (Huangfu et al., 2008)—was expressed for 72 h (in CCD1079Sk cells) to 96 h (in MEFs) at levels similar to or higher levels as in NTERA cells, an embryonic carcinoma cell line—SOX2 expression was detectable for 48 h (in CCD1079Sk cells) to 72 h (in MEFs) (FIG. 8) and (v) MYC and KLF4 were expressed at least 24 h (in CCD1079Sk cells) and 48 h (in MEFs). For both TF short half-lives are published (Chen et al., 2005; Sears et al., 2000) (FIG. 8).

Since it is well established that all mammalian pluripotent stem cells express alkaline phosphatase (AP) activity and that AP is an early marker of the reprogramming process (Pera et al., 2000; Brambrink et al., 2008, Cell Stem Cell. 7, 151-159; O'Connor et al., 2008), we investigated the induction of AP expression upon a single electroporation of IVT-RNA encoding the four TFs OSKM (15 µg each TF).

We found that 10 days post electroporation about 6% of the cells were stained positive for AP as revealed by FACS analysis (FIG. 9). These data match to data published recently showing that 3 days expression of the four TFs OSKM in a doxocyclin-inducible system leads to about 5% AP-positive cells (Brambrink et al., 2008). As mentioned above, a single electroporation leads also to an expression of 3-4 days.

Nevertheless a single electroporation was not sufficient to induce the growth of iPS colonies. This is in accordance to recently published data showing that the induction of AP is reversible and TFs need to be expressed at least 12 days to complete the reprogramming process (Brambrick et al, 2008). On the basis of the time course experiments (FIG. 8) CCD1079Sk cells and MEFs were therefore repeatedly electroporated every 48 h, which means that 6 electroporations are required to ensure at least 12 days of TF expression.

After different time points we stained the cells for the early reprogramming marker AP and analyzed by fluorescence microscopy. Additionally we isolated total RNA from cells just prior each electroporation and evaluated mRNA-expression of endogenous human and murine ES cell markers by quantitative real-time PCR. We included the HDAC-inhibitor VPA in our study because it has been demonstrated that VPA enhances the reprogramming efficiency (Huangfu et al., 2008).

We found that:
(i) cells were reproducible stained positive for AP. AP was induced even at earlier time points as analyzed in the first experiment (4 to 7 days). The amount of IVT-RNA resulting in AP positivity reached from as less as 1.25 µg per TF to 5 µg per TF (FIGS. 10 and 11),
(ii) the addition of VPA greatly increases the percentage of AP-positive MEFs electroporated with IVT-RNA encoding the four TFs OSKM (FIG. 11),
(iii) human and murine ES cell markers that further underline the reprogramming process have been induced: endogenous human OCT4 (FIG. 12), human and murine TERT (telomerase reverse transcriptase) (FIG. 12-14), human GDF3 (growth differentiation factor 3) (FIGS. 12 and 13) and human DPPA4 (developmental pluripotency associated 4) (FIG. 13). As for AP addition of VPA increased the induction of human and murine ES cell marker (FIG. 12-14) and
(iv) repetitive electroporation is associated with a loss of cell viability which became apparent only after the second electroporation. The viability further decreased with every following electroporation.

The addition of previously not electroporated cells (serving as "carrier" cells) during the 4th and 6th electroporation turned out to rescue the electroporated cells (FIG. 14A).

We found that a large number of cells remained viable after the last electroporation. This enabled us to plate these cells onto irradiated MEF feeder cells. The outgrowth of pluripotent colonies from these cells is still under investigation.

Taken together our data show that the electro-transfer of IVT-RNA encoding TFs regulating stem cell pluripotency into somatic cells successfully initiates the reprogramming process. It is expected that the problem of limited viability of the cells will be improved by reducing the time of TF expression necessary to reprogram the cells or increasing the survival of the cells during electroporation.

The following measures are expected to reduce the duration of reprogramming:
(i) It has been recently published that keratinocytes are more rapidly and more efficiently reprogrammed to pluripotent cells than fibroblasts (Aasen et al., 2008, Nat. Biotechnol. 26, 1276-84). Therefore, it is expected that by using keratinocytes such as primary keratinocytes ("normal human epidermal keratinocytes; Promocell, Heidelberg, Germany) a reduced number of electroporations will be sufficient to cover the required expression period.
(ii) It has recently been published that the expression of proteins that are known to immortalize cells, hTERT and SV40 large-T antigen, enhance the efficiency and pace of reprogramming (Park et al., 2008, Nature Protocols 3, 1180-1186; Mali et al., 2008). Therefore, addition of IVT-RNA encoding such proteins such as IVT-RNA encoding codon optimized large-T antigen to the TF-cocktail is expect to provide a beneficial effect.

Figure 4:
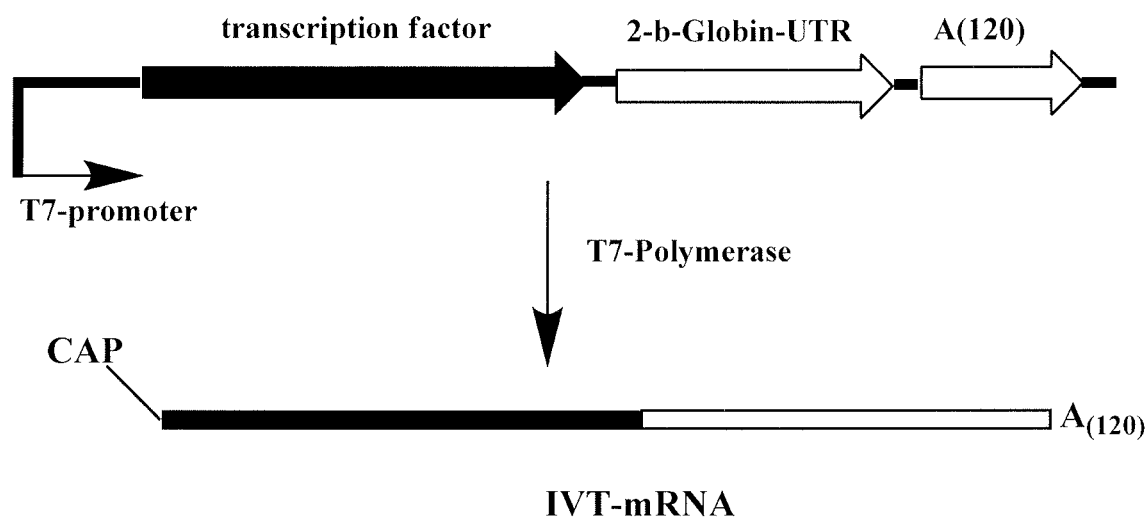

The following measures are expected to increase the survival of the cells:
(i) Voltage and capacity settings of electroporations used herein have been optimized for maximal expression levels after one electroporation. However, even milder conditions resulted in similar percentages of transfected cells with slightly reduced expression levels as monitored by the mean fluorescence of GFP (FIG. 4). Therefore, the settings should be further optimized regarding survival after repeated electroporations without accepting transfection efficiency lower than 75%.
(ii) Our results have shown that human fibroblasts become and remain AP positive for at least 10 days after a single electroporation which is twice or three times longer than the expression of the exogenous TFs. We noted in our time course experiments that human fibroblast start to recover from electroporation induced damage after about 96 hours. Therefore we reason that the frequency of electroporations might be raised to 96 or 120 hours to allow a better recovery of the cells without impairing the reprogramming process.
(iii) Besides the modifications in electroporation conditions and frequencies, an increased survival can also be obtained by inhibiting apoptosis by preventing upregulation of the pro-apoptotic protein p53. To this aim we will add the human papilloma virus 16 transforming protein E6 (HPV-16 E6) to our TF-cocktail. E6 inhibits apoptosis by inducing the poly-ubiquitinylatuion and proteasomal degradation of p53 and by interfering with other pro-apoptotic proteins (Bak, FADD, procaspase-8). Furthermore it induces the expression of hTERT and cooperates positively with c-MYC (Ristriani et al., 2008; Narisawa-Saito & Kiyono 2007).

(iv) In addition we will increase the half-life of the MYC protein by introducing a stabilizing point mutation (Thr-58 to Ala-58) that is found in Burkitt's lymphoma and has been described previously (Sears et al., 2000; Gregory & Hann 2000).

(v) We will functionally delete a destabilizing PEST domain in c-MYC in order to further increase the half-life. PEST-domain deletions have been shown to increase the stability of c-MYC (Gregory & Hann 2000).

The invention claimed is:

1. A cell population which comprises (i) RNA-transfected somatic cells subjected to electroporation, the RNA-transfected somatic cells containing in vitro transcribed mRNA encoding OCT4, SOX2, KLF4 and c-MYC, wherein the mRNA comprises a 5'-Cap structure and wherein the RNA-transfected cells express alkaline phosphatase and endogenous OCT4, and (ii) somatic cells not subjected to electroporation.

2. The cell population in accordance with claim 1, wherein the RNA-transfected somatic cells are human cells transfected with RNA.

3. The cell population in accordance with claim 2, wherein the human cells are adult human dermal fibroblasts transfected with RNA.

4. The cell population in accordance with claim 1, wherein the somatic cells subjected to electroporation are fibroblasts.

5. The cell population in accordance with claim 1, wherein the RNA-transfected somatic cells express endogenous OCT4 for at least 7 days.

6. The cell population in accordance with claim 1, wherein the RNA-transfected somatic cells are fibroblasts deposited at American Type Culture Collection under Catalog No. CCL-186 and subsequently transfected with RNA.

7. The cell population in accordance with claim 1, wherein the RNA-transfected somatic cells are fibroblasts deposited at American Type Culture Collection under Catalog No. CRL-2097 and subsequently transfected with RNA.

8. The cell population in accordance with claim 1, wherein the RNA-transfected somatic cells are derived by RNA-transfection of fibroblasts deposited at American Type Culture Collection under Catalog No. CCL-186.

9. The cell population in accordance with claim 1, wherein the RNA-transfected somatic cells are derived by RNA-transfection of fibroblasts deposited at American Type Culture Collection under Catalog No. CRL-2097.

\* \* \* \* \*